US012751724B2

(12) United States Patent
Carusillo et al.

(10) Patent No.: US 12,751,724 B2
(45) Date of Patent: Oct. 6, 2026

(54) SURGICAL DRILL BIT HAVING AN IDENTIFICATION FEATURE

(71) Applicant: Stryker Corporation, Portage, MI (US)

(72) Inventors: Steven J. Carusillo, Kalamazoo, MI (US); Rahul Sharma, Gurgaon (IN); Brendan Schneider, Portage, MI (US); Trevor Jonathan Lambert, Portage, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/914,490

(22) Filed: Oct. 14, 2024

(65) Prior Publication Data

US 2025/0032130 A1 Jan. 30, 2025

Related U.S. Application Data

(63) Continuation of application No. 17/611,481, filed as application No. PCT/US2020/033288 on May 15, 2020, now Pat. No. 12,133,654.
(Continued)

(51) Int. Cl.
*A61B 17/16* (2006.01)

(52) U.S. Cl.
CPC ................................ *A61B 17/1615* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| | | | |
|---|---|---|---|
| 2,763,935 | A | 9/1956 | Whaley et al. |
| 3,837,661 | A | 9/1974 | Phillippi |

(Continued)

FOREIGN PATENT DOCUMENTS

| | | | |
|---|---|---|---|
| AU | 2015312037 | A1 | 3/2017 |
| AU | 2014346458 | B2 | 11/2018 |

(Continued)

OTHER PUBLICATIONS

Demsey, Daniel et al., "Feasibility of Using Opticat Sensing to Measure Bore Depth in Surgical Bone Drilling", 17th Annual Meeting of the International Society for Computer Assisted Orthopaedic Surgery, CAOS 2017, 7 pages.

(Continued)

*Primary Examiner* — Eric S Gibson
(74) *Attorney, Agent, or Firm* — Howard & Howard Attorneys PLLC

(57) ABSTRACT

A surgical drill bit assembly for use on a surgical drill. The surgical drill bit assembly includes a shank extending between a proximal end and a distal end along an axis. The surgical drill bit assembly also includes a cutting tip portion adjacent to the distal end of the shank. The surgical drill bit assembly also includes a sleeve disposed about at least a portion of the shank. The sleeve includes a non-magnetic material and an identification feature for identifying a configuration of the cutting tip portion. The identification feature includes a magnetic material. The magnetic material is dispersed in the non-magnetic material.

16 Claims, 16 Drawing Sheets

Related U.S. Application Data

(60) Provisional application No. 62/848,038, filed on May 15, 2019, provisional application No. 62/848,029, filed on May 15, 2019.

(58) Field of Classification Search
CPC ............ A61B 17/1622; A61B 17/1624; A61B 17/1626; A61B 17/1628; A61B 17/1631; A61B 90/06; A61B 90/90; A61B 90/98; A61B 2090/062
See application file for complete search history.

(56) References Cited

U.S. PATENT DOCUMENTS 3,897,166 A 7/1975 Adams
4,310,269 A 1/1982 Neu et al.
4,359,906 A 11/1982 Cordey
4,688,970 A 8/1987 Eckman
4,705,038 A 11/1987 Sjostrom et al.
4,752,161 A 6/1988 Hill
4,820,962 A 4/1989 Millauer
5,071,293 A 12/1991 Wells
5,200,747 A 4/1993 Betz et al.
5,257,531 A 11/1993 Motosugi et al.
5,269,794 A 12/1993 Rexroth
RE34,556 E 3/1994 Sjostrom et al.
5,499,984 A 3/1996 Steiner et al.
5,667,509 A 9/1997 Westin
5,749,885 A 5/1998 Sjostrom et al.
5,821,859 A 10/1998 Schrott et al.
5,838,222 A 11/1998 Al-Rawi
5,895,389 A 4/1999 Schenk et al.
6,033,409 A 3/2000 Allotta
6,096,042 A 8/2000 Herbert
6,223,137 B1 4/2001 McCay et al.
6,336,931 B1 1/2002 Hsu et al.
6,371,379 B1 4/2002 Dames et al.
6,382,977 B1 5/2002 Kumar
6,391,005 B1 5/2002 Lum et al.
6,394,806 B1 5/2002 Kumar
6,514,258 B1 2/2003 Brown et al.
6,562,055 B2 5/2003 Walen
6,565,293 B2 5/2003 Desmoulins
6,591,698 B1 7/2003 Carlsson et al.
6,620,101 B2 9/2003 Azzam et al.
6,665,948 B1 12/2003 Kozin et al.
6,719,962 B2 4/2004 Day et al.
6,748,273 B1 6/2004 Obel et al.
6,783,533 B2 8/2004 Green et al.
6,786,683 B2 9/2004 Schaer et al.
6,863,136 B2 3/2005 Bar-Cohen et al.
7,060,071 B2 6/2006 Steiger
7,141,074 B2 11/2006 Fanger et al.
7,163,542 B2 1/2007 Ryan
7,188,431 B2 3/2007 Herrmann et al.
7,258,546 B2 8/2007 Beier et al.
7,431,682 B2 10/2008 Zeiler et al.
7,482,819 B2 1/2009 Wuersch
7,517,351 B2 4/2009 Culp et al.
7,580,743 B2 8/2009 Bourlion et al.
7,681,659 B2 3/2010 Zhang et al.
7,740,425 B2 6/2010 Zeiler et al.
7,748,273 B2 7/2010 Halevy-Politch et al.
7,771,143 B2 8/2010 Bharadwaj et al.
7,848,799 B2 12/2010 Herndon
8,092,457 B2 1/2012 Oettinger et al.
8,241,229 B2 8/2012 Herndon
8,249,696 B2 8/2012 Fisher et al.
8,402,829 B2 3/2013 Halevy-Politch et al.
8,419,746 B2 4/2013 Bourlion et al.
8,460,297 B2 6/2013 Watlington et al.
8,463,421 B2 6/2013 Brett et al.
8,480,682 B2 7/2013 Howlett et al.
8,486,119 B2 7/2013 Bourlion
8,511,945 B2 8/2013 Apkarian et al.
8,535,342 B2 9/2013 Malackowski et al.
8,603,148 B2 12/2013 Raven, III et al.
8,641,674 B2 2/2014 Bobroff et al.
8,821,493 B2 9/2014 Anderson
8,876,444 B1 11/2014 Chanturidze
8,894,654 B2 * 11/2014 Anderson ............ B25B 21/002
173/176
D719,594 S 12/2014 Leugers
8,936,468 B2 1/2015 Ranck et al.
D722,627 S 2/2015 Leugers
8,970,207 B2 * 3/2015 Baumgartner ......... A61B 90/06
324/207.2
8,974,227 B2 3/2015 Magnusson et al.
D727,985 S 4/2015 Leugers
9,033,707 B2 5/2015 Dricot
D732,364 S 6/2015 Rinaldis et al.
9,204,885 B2 * 12/2015 McGinley ............ A61B 17/162
9,256,988 B2 2/2016 Wenger et al.
9,289,219 B2 3/2016 Kumar
9,326,832 B2 5/2016 Zuker et al.
9,345,487 B2 5/2016 Herndon et al.
D759,244 S 6/2016 Leugers
D759,245 S 6/2016 Leugers
9,358,016 B2 * 6/2016 McGinley ............ A61B 17/162
9,370,372 B2 * 6/2016 McGinley .......... A61B 17/1626
9,468,445 B2 10/2016 McGinley et al.
9,492,181 B2 * 11/2016 McGinley ............ A61B 17/162
9,526,511 B2 12/2016 Anderson
9,554,807 B2 1/2017 McGinley et al.
9,566,121 B2 2/2017 Staunton et al.
9,649,141 B2 5/2017 Raven, III et al.
9,826,984 B2 * 11/2017 McGinley ............ A61B 17/142
9,877,734 B2 * 1/2018 Anderson .......... A61B 17/1622
9,914,192 B2 * 3/2018 Rola .................. B23Q 17/2457
10,149,686 B2 * 12/2018 Anderson .......... A61B 17/1626
10,159,495 B1 12/2018 Lambert
10,245,043 B2 * 4/2019 Xie ...................... A61B 17/162
10,321,920 B2 6/2019 McGinley
10,321,921 B2 * 6/2019 McGinley .......... A61B 17/1626
10,368,935 B2 * 8/2019 Suzuki ..................... A61N 7/00
10,398,453 B2 * 9/2019 McGinley .............. A61B 90/30
10,661,428 B2 5/2020 Baskar et al.
10,682,205 B2 * 6/2020 Garbus .................. A61B 34/25
10,695,074 B2 * 6/2020 Carusillo ........... A61B 17/1628
10,736,643 B2 8/2020 Anderson et al.
10,736,644 B2 * 8/2020 Windolf ............. A61B 17/1622
10,893,873 B2 * 1/2021 McGinley .......... A61B 17/1626
10,925,619 B2 * 2/2021 Anderson ........... B25B 23/0064
11,058,436 B2 * 7/2021 McGinley ............ A61B 17/142
11,317,927 B2 * 5/2022 Carusillo ............... A61B 90/06
11,382,639 B2 * 7/2022 Miller ................ A61B 17/1624
11,426,180 B2 * 8/2022 O'Brien ............... A61B 17/162
11,478,255 B2 * 10/2022 Windolf ............. A61B 17/1626
11,517,326 B1 * 12/2022 Sharma ............. A61B 17/1615
11,540,841 B2 * 1/2023 Carusillo ........... A61B 17/1626
11,812,977 B2 * 11/2023 Carusillo ........... A61B 17/1615
11,857,204 B2 * 1/2024 Windolf ............. A61B 17/1633
11,896,239 B2 * 2/2024 Carusillo ........... A61B 17/1615
12,133,654 B2 * 11/2024 Carusillo ........... A61B 17/1615
2003/0199856 A1 * 10/2003 Hill ........................ A61B 17/16
606/1
2004/0059317 A1 3/2004 Hermann
2004/0215395 A1 10/2004 Strasser et al.
2005/0116673 A1 6/2005 Carl
2005/0131415 A1 6/2005 Hearn et al.
2005/0131416 A1 6/2005 Jansen et al.
2005/0171553 A1 8/2005 Schwarz et al.
2006/0161136 A1 7/2006 Anderson et al.
2006/0241628 A1 10/2006 Parak
2006/0259055 A1 * 11/2006 Thorne ................ A61B 17/162
606/180
2007/0206996 A1 9/2007 Bharadwaj et al.
2009/0221922 A1 9/2009 Lec et al.
2009/0245956 A1 10/2009 Apkarian et al.
2009/0297284 A1 12/2009 Brown et al.
2009/0326537 A1 12/2009 Anderson
2010/0034605 A1 2/2010 Huckins et al.
2010/0167233 A1 7/2010 Dricot
2011/0020084 A1 1/2011 Brett et al.

(56) References Cited

U.S. PATENT DOCUMENTS

2011/0089248 A1 4/2011 Deng et al.
2011/0230886 A1 9/2011 Gustilo et al.
2011/0245833 A1* 10/2011 Anderson .......... A61B 17/1628 606/80
2011/0282188 A1 11/2011 Burnside et al.
2011/0315414 A1 12/2011 Kuntner et al.
2012/0123417 A1 5/2012 Smith
2012/0310247 A1 12/2012 Hsieh
2013/0138106 A1 5/2013 Kumar
2013/0307529 A1 11/2013 Baumgartner
2013/0338669 A1 12/2013 Brianza et al.
2014/0018810 A1 1/2014 Knape et al.
2014/0046332 A1 2/2014 Premanathan et al.
2014/0114316 A1 4/2014 Xu et al.
2014/0148808 A1 5/2014 Inkpen et al.
2014/0222003 A1 8/2014 Herndon et al.
2014/0275955 A1 9/2014 Crawford et al.
2014/0371751 A1 12/2014 Thomas
2014/0371752 A1 12/2014 Anderson
2015/0066030 A1* 3/2015 McGinley .............. A61B 90/30 606/79
2015/0066035 A1* 3/2015 McGinley ............ A61B 17/162 606/80
2015/0066036 A1* 3/2015 McGinley ............ A61B 17/162 606/80
2015/0066037 A1* 3/2015 McGinley .......... A61B 17/1628 606/80
2015/0066038 A1* 3/2015 McGinley .......... A61B 17/1615 606/80
2015/0080966 A1* 3/2015 Anderson ........... B25B 23/0064 606/280
2015/0134010 A1 5/2015 Zlotolow
2015/0141999 A1 5/2015 McGinley et al.
2015/0148805 A1 5/2015 McGinley et al.
2015/0148806 A1 5/2015 McGinley et al.
2015/0272608 A1* 10/2015 Gladstone .......... A61B 17/1622 606/167
2016/0051265 A1 2/2016 Jones et al.
2016/0120553 A1* 5/2016 Xie ...................... A61B 17/162 606/80
2016/0128704 A1 5/2016 McGinley et al.
2016/0192974 A1 7/2016 Clain
2016/0206328 A1 7/2016 Lo et al.
2016/0278802 A1 9/2016 Cihak et al.
2017/0007289 A1 1/2017 McGinley et al.
2017/0105811 A1* 4/2017 Garbus .................. A61B 90/98
2017/0128081 A1 5/2017 McGinley
2017/0143396 A1 5/2017 McGinley et al.
2017/0143440 A1 5/2017 McGinley et al.
2017/0290602 A1 10/2017 Germain et al.
2017/0303990 A1 10/2017 Benamou et al.
2017/0340374 A1 11/2017 Xie et al.
2018/0221032 A1 8/2018 Garcia et al.
2021/0186524 A1* 6/2021 Carusillo ........... A61B 17/1622
2022/0241045 A1* 8/2022 Carusillo ........... A61B 17/1615
2023/0338044 A1* 10/2023 Sharma .............. A61B 17/1633
2023/0414228 A1* 12/2023 Sharma .............. A61B 17/1633
2025/0032130 A1* 1/2025 Carusillo ........... A61B 17/1633

FOREIGN PATENT DOCUMENTS

AU 2014315652 B2 5/2019
CA 3140391 A1 * 11/2020 ............. A61B 90/98
CN 1193388 A 9/1998
CN 101530341 A 9/2009
CN 204394613 U 6/2015
CN 206526112 U 9/2017
CN 108143484 A 6/2018
CN 114126513 A * 3/2022 ............. A61B 90/98
CN 114760938 A * 7/2022 ......... A61B 17/1622
CN 116710002 A * 9/2023 ......... A61B 17/1622
EP 1330192 A2 7/2003
EP 1374784 A1 1/2004
EP 2156794 A1 * 2/2010 ....... A61B 17/32002
EP 2800531 A1 11/2014
EP 3041419 B1 1/2019
EP 3065650 B1 1/2019
EP 2647339 B1 4/2020
GB 2491524 A * 12/2012 ....... A61B 17/32002
JP S6262509 A 3/1987
JP S6357149 A 3/1988
JP 2000507839 A 6/2000
JP 1559620 S 9/2016
JP 2018516036 A 6/2018
JP 2022532407 A * 7/2022 ......... A61B 17/1626
JP 2022551714 A * 12/2022 ......... A61B 17/1622
JP 2023550408 A * 12/2023 ......... A61B 17/1622
KR 20100050763 A 5/2010
KR 20220010732 A * 1/2022 ............. A61B 90/98
KR 20220079659 A * 6/2022 ......... A61B 17/1622
WO 0166024 A1 9/2001
WO 03013372 A2 2/2003
WO 2007002230 A1 1/2007
WO 2009158115 A1 12/2009
WO 2010028046 A1 3/2010
WO 2013029582 A1 3/2013
WO 2013098555 A1 7/2013
WO 2013173138 A1 11/2013
WO 2015006296 A1 1/2015
WO 2015034562 A1 3/2015
WO 2015070159 A1 5/2015
WO 2016036756 A1 3/2016
WO 2016049467 A1 3/2016
WO 2016067739 A1 5/2016
WO 2016199152 A1 12/2016
WO 2017040783 A1 3/2017
WO 2017075044 A1 5/2017
WO 2017075060 A1 5/2017
WO 2017075224 A1 5/2017
WO 2017078754 A1 5/2017
WO 2017083992 A1 5/2017
WO 2018140646 A1 8/2018
WO 2018169565 A1 9/2018
WO 2018183002 A1 10/2018
WO 2019035096 A1 2/2019
WO 2019040381 A1 2/2019
WO WO-2020232413 A3 * 12/2020 ......... A61B 17/1615
WO WO-2021072373 A1 * 4/2021 ......... A61B 17/1622
WO WO-2022109135 A1 * 5/2022 ......... A61B 17/1622

OTHER PUBLICATIONS

English language abstract and machine-assisted English translation for CN 101530341 extracted from espacenet.com database on Apr. 15, 2020, 7 pages.
English language abstract and machine-assisted English translation for CN 108143484 A extracted from espacenet.com database on Sep. 12, 2024, 7 pages.
English language abstract and machine-assisted English translation for CN 204394613 extracted from espacenet.com database on Apr. 15, 2020, 7 pages.
English language abstract and machine-assisted English translation for CN 206526112 U extracted from espacenet.com database on Sep. 12, 2024, 9 pages.
English language abstract and machine-assisted English translation for JP 2018-516036 A extracted from espacenet.com database on Nov. 18, 2021, 80 pages.
English language abstract and machine-assisted English translation for JPS 62-62509 A extracted from espacenet.com database on Dec. 30, 2023, 4 pages.
English language abstract and machine-assisted English translation for KR 20100050763 extracted from espacenet.com database on Apr. 15, 2020, 6 pages.
English language abstract and machine-assisted English translation for WO 2013/029582 extracted from espacenet.com database on Apr. 15, 2020, 10 pages.
English language abstract for CN 1193388 A extracted from espacenet.com database on Sep. 12, 2024, 2 pages.
English language abstract for EP 1 330 192 extracted from espacenet.com database on Apr. 15, 2020, 1 page.

(56) References Cited

OTHER PUBLICATIONS

English language abstract for JP 2000-507839 A extracted from espacenet.com database on Dec. 30, 2023, 1 page.
English language abstract for WO 01/66024 extracted from espacenet.com database on Mar. 1, 2018, 2 pages.
English language abstract for WO 2016/067739 A1 extracted from espacenet.com database on Dec. 30, 2023, 2 pages.
English language abstract not found for JP 1559620; however, see English language equivalent USD 732,364. Original document unavailable, 1 page.
International Search Report for Application No. PCT/IB2018/056251 dated Jan. 3, 2019, 4 pages.
International Search Report for Application No. PCT/US2020/033288 dated Dec. 11, 2020, 4 pages.
McGinley Orthopaedic Innovations, "IntelliSense Drill Brochure", 2015, 4 pages.
Partial International Search Report for Application No. PCT/US2020/033288 dated Sep. 10, 2020, 2 pages.
Stryker, "Cordless Driver 3 Accessories Brochure", 2017, 2 pages.
English language abstract and machine-assisted English translation for JPS 63-57149 A extracted from espacenet.com database on Dec. 1, 2025, 6 pages.

* cited by examiner

AX
6A
6C
70
180
66, 66a
182
65
177, 177a
176
181
177a
177d
210
208
183A
D1

SURGICAL DRILL BIT HAVING AN IDENTIFICATION FEATURE

RELATED APPLICATIONS

The subject patent application is a continuation of U.S. patent application Ser. No. 17/611,481, filed on Nov. 15, 2021, which is the national phase of International Application No. PCT/US2020/033288, filed on May 15, 2020, which claims priority to and all the benefits of U.S. Provisional Patent Application No. 62/848,029, filed on May 15, 2019 and U.S. Provisional Patent Application No. 62/848,038, filed on May 15, 2019, which are hereby incorporated herein by reference in their entirety.

BACKGROUND

One type of powered surgical tool, or powered surgical system, used in orthopedic surgery is the surgical drill. This type of tool includes a housing that contains a motor. A coupling assembly or coupling, also part of the drill, releasably holds a drill bit to the motor so that, upon actuation of the motor, the drill bit rotates. As implied by its name, a surgical drill drills bores in the workpiece, such as tissue, against which the drill bit is applied. One type of surgical procedure in which it is necessary to drill a bore is a trauma procedure to repair a broken bone. In this type of procedure, an elongated rod, sometimes called a nail, is used to hold the fractured sections of the bone together. To hold the nail in place, one or more bores are driven into the bone. These bores are positioned to align with complementary holes formed in the nail. A screw is inserted in each aligned bore and nail hole. The screws hold the nail in the proper position relative to the bone.

In another type of procedure, an implant, or workpiece, known as a plate is secured to the outer surfaces of the fractured sections of a bone to hold the sections together. Screws hold the plate to the separate sections of bone. To fit a screw that holds a plate to bone it is necessary to first drill a bore to receive the screw.

As part of a procedure used to drill a screw-receiving bore in a bone, it is desirable to know the end-to-end depth of the bore. This information allows the surgeon to select the size of a screw that is fitted in the bore hole. If the screw is too short, the screw may not securely hold the nail into which the screw is inserted in place. If the screw is too long, the screw can extend an excessive distance out beyond the bone. If the screw extends an excessive distance beyond the bone, the exposed end of the screw can rub against the surrounding tissue. If this event occurs, the tissue against which the screw rubs can be damaged. Accordingly, an integral part of many bone bore-forming procedures is the measuring of the depth of the bore.

The present disclosure addresses some of these issues.

DETAILED DESCRIPTION

Figure 1:
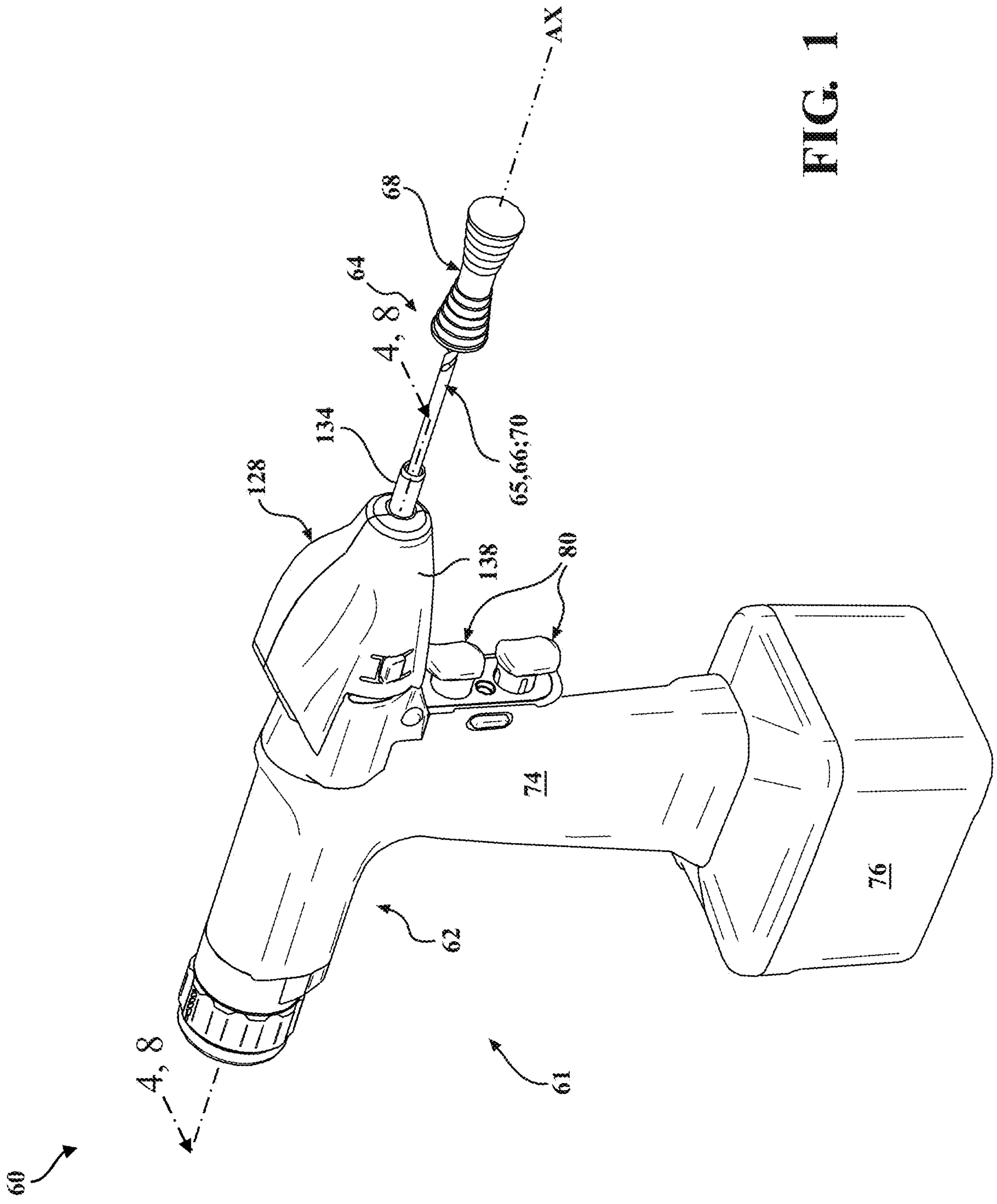
FIG. 1 is perspective view of a surgical system comprising a surgical instrument and end effector, the end effector shown having a drill bit having an identification feature and a tip protector according to one configuration.
Figure 2:
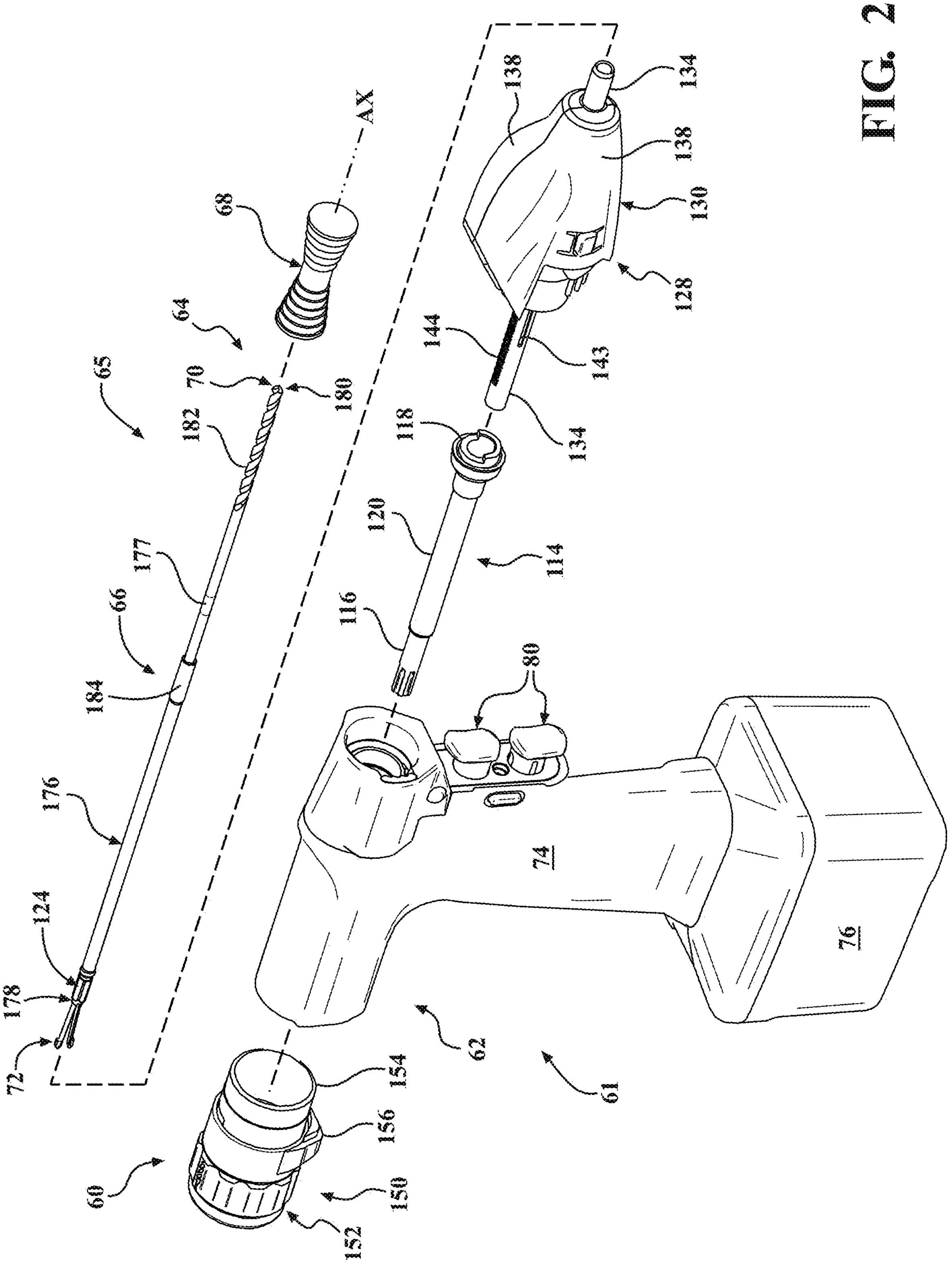
FIG. 2 is a partially-exploded perspective view of the surgical system of FIG. 1, with the surgical instrument shown having a measurement module, a drive assembly, and a release mechanism spaced from a handpiece body, and with the end effector removed from the surgical instrument and shown with the tip protector spaced from a distal cutting tip portion of the drill bit.

With reference to the drawings, where like numerals are used to designate like structure throughout the several views, a surgical system, or surgical drill system, is shown at 60 in FIGS. 1-2 for performing an operational function that is typically associated with medical and/or surgical procedures. In some configurations the surgical drill system 60 may also be referred to as a surgical handpiece system. In the representative configuration illustrated herein, the surgical drill system 60 is employed to facilitate penetrating a workpiece, such as tissue or bone of a patient. As used herein, unless otherwise indicated, the term workpiece is understood to alternatively refer to tissue and/or bone. To this end, the illustrated configuration of the surgical drill system 60 comprises a surgical drill 61 that comprises a handpiece 62, alternatively referred to as a handheld surgical instrument 62, and an end effector, generally indicated at 64, coupled to the handpiece 62. The end effector 64, in turn, comprises a drill bit assembly 65 including one or more replaceable drill bits 66 and may also include a tip protector 68. Devices other than surgical drills may also be used with the features described herein, such as surgical drivers. As such, the end effector 64 may comprise a bit configured to drive a surgical implant, such as a screw. Alternatively still, the end effector may be implemented as a reamer.

As is best depicted in FIG. 2, each respective one of the one or more drill bits 66 (a single representative drill bit 66 is illustrated in FIG. 2), when respectively coupled to the handpiece 62, extends generally longitudinally along an axis AX (i.e., the longitudinal axis AX or axis AX) between a cutting tip portion, generally indicated at 70, and an insertion portion, generally indicated at 72. The cutting tip portion 70 is configured to engage the workpiece, and the insertion portion 72 is configured to facilitate releasable attachment of the drill bit 66 to the handpiece 62. Various configurations of the insertion portion are contemplated to enable coupling of the drill bit 66 to the handpiece 62, such as various grooves, slots, and other geometries. One exemplary configuration of an insertion portion can be found in U.S. Pat. No. 10,159,495, which is hereby incorporated by reference in its entirety. It is contemplated that there may be other configurations to facilitate attachment of the drill bit 66 to the handpiece 62.

As also shown in FIG. 2, each respective one of the one or more drill bits 66 extending along the axis AX from a proximal end to a distal end. Each of the drill bits 66 comprises a shank, generally indicated at 176, which extends along the axis AX between a proximal end 178 and a distal end 180. A distal portion of the shank 176 adjacent the distal end 180 of the shank 176 may define flutes 182 which may be helically disposed about the axis AX and extend to the cutting tip portion 70 of the drill bit 66 to promote workpiece, such as tissue, penetration (see FIG. 2). In the illustrated configuration, the drill bit 66 may also be provided with a bearing region 184 coupled to the shank 176 between the proximal end 178 and the distal end 180. In many configurations the bearing region 184 is integral with the shank 176. The bearing region 184 is sized so as to be received within and rotate relative to a measurement cannula 134 of a measurement module 128 that may be coupled to the handpiece (discussed in greater detail further below). Here, the bearing region 184 may define a "stepped" outer region of the shank 176 that affords rotational support along the length of the drill bit 66, and may have a larger diameter than adjacent distal and proximal regions of the shank 176 in the illustrated configuration. However, it will be appreciated that the bearing region 184 of the shank 176 of the drill bit 66 could configured in other ways without departing from the scope of the present disclosure. Furthermore, while described as a drill bit 66 in the present disclosure, it is also contemplated that the drill bit 66 could have similar features and be configured as another suitable end effector, or rotary end-effector, such as a bur or reamer.

A plurality of configurations of the drill bit 66 may be configured to be couple to the surgical handpiece 62. Each of the plurality of drill bits 66 (representative drill bits 66*a*, 66*b*, 66*c* are shown in FIGS. 6, 7, 11 and 12) may be different from one another in at least one feature or characteristic. These differing performance features or characteristics may result in a variation in the performance of the surgical drill system 60 during use depending on which of the drill bits 66 is used. Said differently, in the configurations illustrated in FIGS. 6A-6D, 7-7B, 11-11A, and 12-12B each drill bit 66*a*, 66*b*, 66*c* has a unique combination of performance features or characteristics). In particular, drill bits 66 are contemplated as having different cross-sectional areas or diameters at or near the distal end 180 to allow for the drilling of larger or smaller holes within the bone during use. For example, the drill bit 66*b* of FIG. 11 may have a larger diameter D2 adjacent the distal end 180 than the diameter D1 of the drill bit 66*a* of FIGS. 6 and 6C. Further, the diameter D3 of the drill bit 66*c* of FIG. 12B may be different from both diameters D1, D2 of the drill bits 66*a*, 66*b*.

Another performance feature is the arrangement of the helical flutes 182. The helically disposed flutes 182 may have varying helical structure or groove depths that varies the cutting efficiency. In one configuration illustrated in FIG. 12, the drill bit 66*c* has a helical structure 183B having increased number of helixes per unit measure at the distal end 180 is illustrated in FIGS. 12 and 12B as compared to the helical structure 183A of the drill bit 66*a* of FIGS. 6A and 6C and the drill bit 66*b* of FIG. 11). Even still further performance features, the length of the drill bit 66 may vary, depending upon the estimated thickness of the bone on which the surgical drill system 60 is used. For yet another performance feature, the material choice of the drill bit 66 itself may vary, which may affect drilling efficiency or heat transfer of the respective drill bit 66 as compared with the other drill bits 66 for the surgical drill system 60. Another performance feature includes rake angle or point angle of the cutting tip portion 70. In particular, a unique combination of these performance features or characteristics is provided on the respective one drill bit 66 to provide the operator of the surgical drill system 60 with a wide variety of options for penetrating the workpiece. Additionally, these performance features may be identified by the handpiece 62 to perform certain actions during operation as described further below.

To aid the operator in determining which drill bit 66 is coupled to the handpiece 62, an identification feature 177 may also be included on each respective drill bit 66 of the drill bit assembly 65 that identifies the respective drill bit 66 and the. The identification feature 177 is correlated to the performance features associated with each type of drill bit 66 or end effector 64. For example, based on identification feature 177*a* (shown in FIGS. 6, 6A and 6B), the surgical drill 61 can determine that drill bit 66*a* is configured for small bone drilling, i.e., the distal portion of the drill bit 66*a* may have a diameter generally of less than or equal to 2 mm (and used for small bones such as the foot or hand, etc.), whereas based on identification feature 177*b* (shown in FIGS. 11 and 11A), the surgical drill 61 can determine that the drill bit 66*b* is configured for large bone drilling, i.e., the distal portion of the drill bit 66*b* may have a diameter of greater than or equal to about 3.2 mm (and used for longer bones such as femurs), or is configured for bone drilling at drill bit diameters between 2 and 3.2 mm. Still further, based on identification feature 177*c* (shown in FIGS. 12A and 12B), the surgical drill 61 can also determine the associated helical structure of the flutes 182 adjacent the distal end 180 for a more precisely determined drilling profile, along with the respective diameter, of the drill bit 66. From this information, the surgical drill 61 can also balance factors such as cutting efficiency versus temperature and more accurately calculate breakthrough depth (as is described below), thereby improving accuracy. Associated therewith, the operator can more precisely control operation of the surgical drill 61 for drilling a bore based upon knowledge gained from the identification feature 177 regarding the coupled drill bit 66.

As shown in FIGS. 6, 7, 11 and 12, in various configurations, the identification feature 177 may be in the form of one or more magnets 181 that are disposed about the shank 176 between the proximal end 178 and the distal end 180 of the drill bit 66. The one or more magnets 181 may comprise an array of magnets to circumferentially surround the shank 176 of the drill bit 66. Other types of identification features 177 are contemplated, such as grooves, scallops, protrusions on the end effector 64, various types of electronic devices, such as RFID (Radio-frequency Identification), NOVRAM ("Non-Volatile Random Access Memory"), etc. may also be positioned on the end effector 64 to allow the surgical instrument 60 to identify what type of end effector 64 is coupled to the surgical instrument 62. Still further, the identification feature 177 may be in the form of an optical feature 177*a* (see FIGS. 10A-10C), such as a laser etching, laser print, or a label with this optical feature being disposed on or within the shank 176 between the proximal end 178 and the distal end 180 of the drill bit.

Figures 6, 6A, 6B, 6C, 6D:
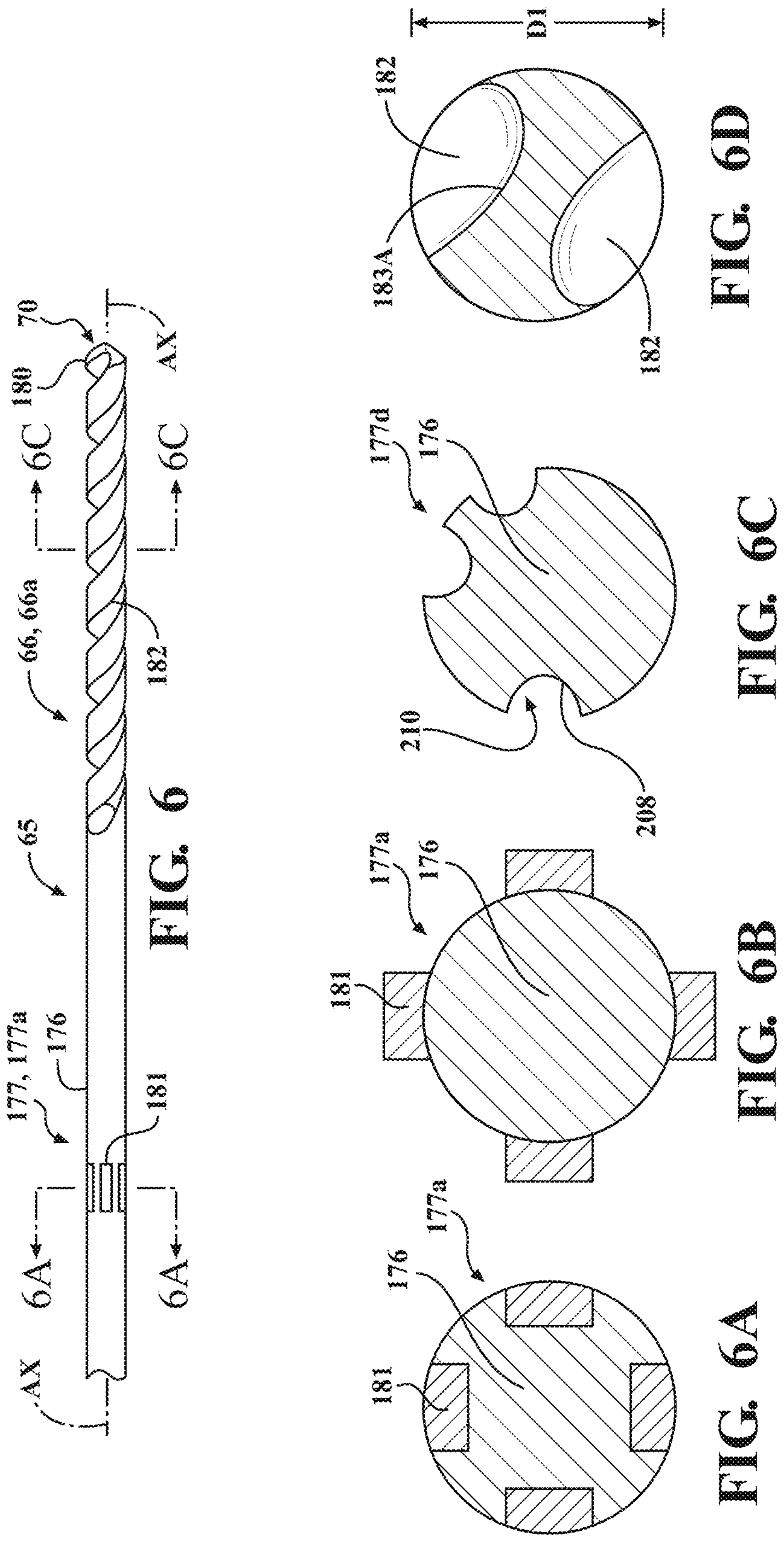
FIG. 6 is a perspective view of the drill bit assembly of FIGS. 1-2 and 4-5 including the identification feature.
FIG. 6A is a section view of the drill bit assembly of FIG. 6 taken along line 6A-6A in accordance with one configuration.
FIG. 6B is a section view of the drill bit assembly of FIG. 6 in accordance with another configuration.
FIG. 6C is a section view of the drill bit assembly of FIG. 6 in accordance with another configuration.
FIG. 6D is a section view of the drill bit assembly of FIG. 6 taken along line 6C-6C.

In configurations utilizing magnets 181 as the identification feature 177, such magnets 181 may be at least partially embedded within the shank 176 (see FIG. 6A, 11A or 12A) or coupled directly to the outer surface of the shank 176 (see FIG. 6B). Alternatively, the magnets 181 may be embedded within a sleeve 179 (see FIG. 7A), or coupled to an external surface of a sleeve 179 (see FIG. 7B), which is disposed about at least a portion of the shank 176 between the proximal end 178 and the distal end 180. The sleeve 179 may include a lumen sized to be disposed over the shank 176 of the drill bit 66. Although the sleeves 179 illustrated in FIGS. 7-7B and FIGS. 15 and 16 comprise tubular structure that surrounds the shank 176 of the drill bit 66, it is contemplated that the sleeve 179 may comprise layer disposed over the shank 176 of the drill bit 66. Further, the sleeve 179 may only partially surround the shank 176 of the drill bit 66.

Figure 7:
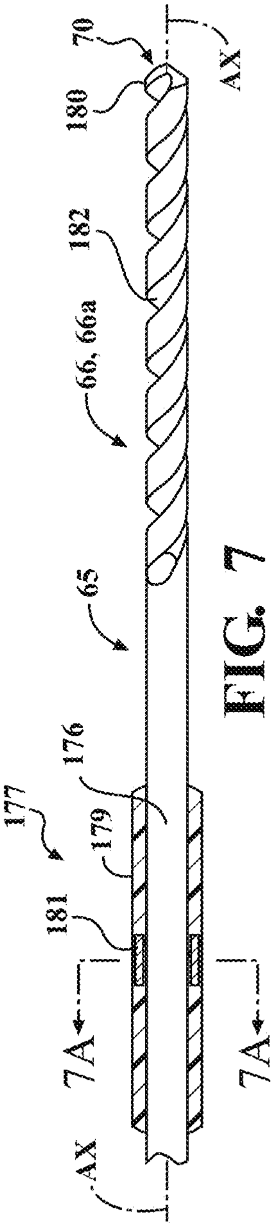
FIG. 7 is a perspective view of the drill bit assembly of FIGS. 1 and 2 including the identification feature coupled to a sleeve.
Figure 7B:
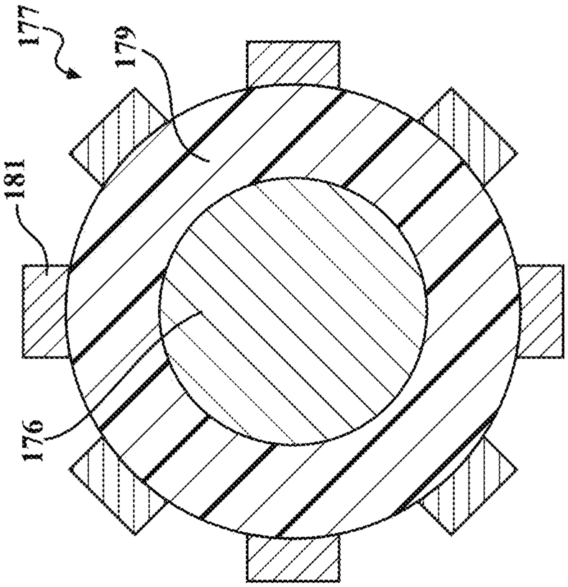
FIG. 7B is a section view of the drill bit assembly of FIG. 7 in accordance with another configuration.

In the illustrations of FIGS. 6B and 7B, the extension of the magnets 181 radially outward from an outer surface of the shank 176 (FIG. 6B), or from an outer surface of the sleeve 179 (FIG. 7B) may be exaggerated for ease of viewing and is not intended to be representative of the relative amount to which the magnets 181 extend radially outward from the respective outer surface of the shank 176 or sleeve 179. Accordingly, it may be preferable that the magnets 181 do not extend a great distance radially outward so as not to affect the rotation of the drill bit 66 during use and for case of insertion within a driving cannula 116 of the handpiece 62.

Figure 11:
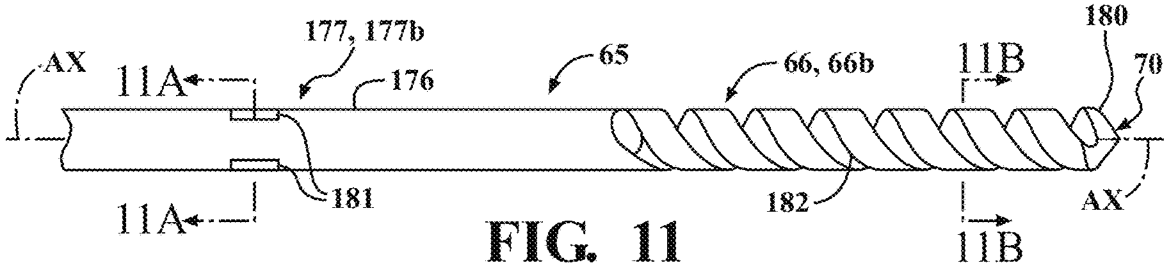
FIG. 11 is a perspective view of a drill bit in an alternative configuration having a larger diameter D2 at a distal end than the diameter D1 of the drill bit of FIG. 6.
Figure 11A:
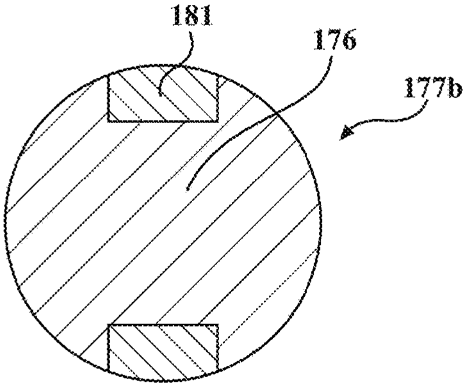
FIG. 11A is a section view of the drill bit assembly of FIG. 11 taken along line 11A-11A in accordance with one configuration.
Figure 11B:
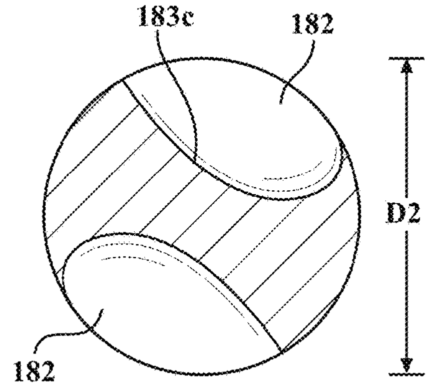
FIG. 11B is a section view of the drill bit assembly of FIG. 11 taken along line 11B-11B.
Figure 12:
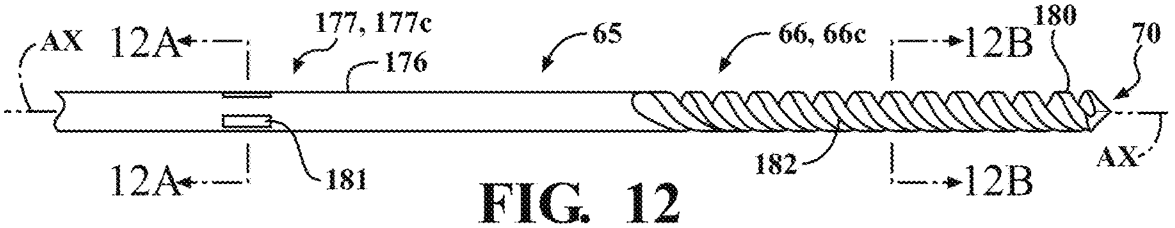
FIG. 12 is a perspective view of a drill bit in an alternative configuration having a varying flute design at a distal end than the drill bit of FIG. 6.
Figure 12A:
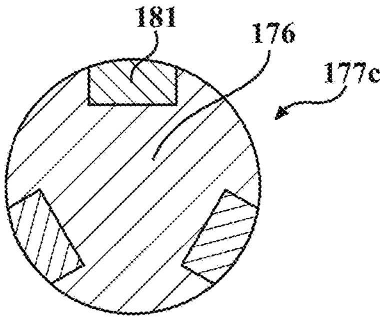
FIG. 12A is a section view of the drill bit assembly of FIG. 12 taken along line 12A-12A in accordance with one configuration.
Figure 12B:
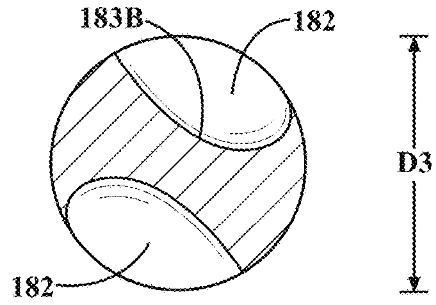
FIG. 12B is a section view of the drill bit assembly of FIG. 12 taken along line 12B-12B in accordance with one configuration.

The location, size, angular spacing, strength, polarity, and number of the one or more magnets 181 in each configuration as shown in FIGS. 6, 7, 11 and 12 are unique for each respective one of the drill bits 66, and thus functions to differentiate each respective drill bit 66 from each other respective drill bit 66. In the examples in FIGS. 6, 7, 11 and 12 provided herein, a single array of equally sized magnets 181, angularly spaced from one another equally about the axis AX of the drill bit 66, are respectfully illustrated as representative configurations of a single array of equally sized, equally angularly spaced magnets 181 for use in the surgical drill instrument 60. The number and angular spacing of the single array of the equally sized one or more magnets 181 may be used to differentiate the various drill bits 66. In the example of FIG. 6, a single array of four equally sized and angularly spaced magnets 181 is shown. FIG. 7 illustrates a single array of eight equally sized and angularly spaced magnets 181. Further, FIG. 11 illustrates a single array of two equally sized and angularly spaced magnets 181, while FIG. 12 illustrates a single array of three equally sized and angularly spaced magnets 181. In another configuration, the one or more magnets 181 may comprise a second array of magnets (not shown) disposed circumferentially about the shank 176 and disposed axially spaced from the first array of magnets. It is contemplated that similar to the first array of magnets, each magnet in the second array of magnets may differ in location, size, angular spacing, strength, or polarity to other magnets in the array. Further, the number of magnets in each array of magnets may be different or the same. Further still, the magnets 181 in each array of magnets may be angularly aligned when viewed from a direction along the axis AX or parallel to the axis AX. It is also contemplated that at least one magnet 181 of one of the arrays is not angularly aligned with a magnet of the other array when viewed in a direction along the axis AX or parallel to the axis AX. In these examples, the sizes and magnetic strengths/directions of the magnets 181 in each Figure may also be the same. While FIGS. 6, 7, 11 and 12 illustrate four unique respective placements of multiple magnets 181 placed in a single array, corresponding to four unique drill bit assemblies 65, alterations in the number, size, spacing, strength, or location of the magnets 181 are contemplated, with each unique combination configured to be different so as to function to differentiate further additional drill bits 66 and corresponding drill bit assemblies 65.

The magnets 181 are formed from magnetic material that collectively generate a magnetic field of a certain strength and direction based upon the unique combination of location, size, spacing, strength and number of magnets 181 disposed on the respective drill bit 66.

In another configuration shown in FIG. 6C, at least a portion of the shank 176 of the drill bit 66 is magnetized and an outer surface 208 may define one or more recesses 210 to establish a non-circular cross-section on a plane perpendicular to the axis AX such that a radial distance between the outer surface 208 and the axis AX varies about the axis AX. The shank 176 is configured to effect variations in the magnetic field during rotation of the shank 176 about the axis AX responsive to the varying radial distances of the outer surface 208 to the axis AX. In this manner, the one or more recesses comprise an identification feature for identifying one or more performance features of the cutting tip portion 70. The sensor 201 may comprise a magnetoresistance sensor to generate a signal responsive to the varying magnetic field while the drill bit 66 is coupled to the handpiece 62 and rotating about the axis AX. In many configurations, the varying radial distance between the outer surface 208 of the shank 176 of the drill bit 66 is distinct from a coupling portion proximal the shank that is configured to engage the surgical drill or handpiece 62 to couple the drill bit 66 to the surgical drill or handpiece 62.

As noted above for similar configurations, the performance features of the cutting tip portion 70 may be selected from a length of the drill bit 66, a material of the drill bit 66, a diameter of a distal end 180 of the shank 176 of the drill bit 66, a cross-sectional area of the drill bit 66, a type of drill bit 66, a rake angle of the drill bit 66, a flute angle of the drill bit 66, and/or a point angle of the drill bit 66.

The one or more recesses 210 of the shank 176 may be further defined as an array of recesses disposed circumferentially about the shank. One recess of the array of recesses may be different in depth, arc length, or combinations thereof than at least one other recess of the array of recesses. Additionally, angular spacing between a first recess of the array of the recesses and a second recess of the array of recesses may be different or the same as angular spacing between the second recess and a third recess of the array of recesses.

In another configuration, the one or more recesses 210 may define a second array of recesses (not shown) disposed circumferentially about the shank 176 and disposed axially spaced from the first array of recesses 210. It is contemplated that similar to the first array of recesses 210, each recess 210 in the second array of recesses 210 may differ in depth, arc length, or combinations thereof to another recess 210 in the array of recesses 210. Further, the number of recesses 210 in each array of recesses 210 may be different or the same. Further still, the recesses 210 in each array of recesses 210 may be angularly aligned when viewed from a direction along the axis AX or parallel to the axis AX. It is also contemplated that at least one recess 210 of one of the arrays of recesses 210 is not angularly aligned with a recess 210 of the other array when viewed in a direction along the axis AX or parallel to the axis AX.

In certain configurations, the magnetic material of the magnets 181 (or the magnetized drill bit 66 in FIG. 6C) is preferably a magnetic material that is temperature sensitive, i.e. a magnetic material that loses some or all of its magnetism when heated to a temperature above its Curie point (i.e., a magnetic material that becomes at least partially demagnetized when heated to a temperature above its Curie point). Preferred magnetic materials suitable for use in the magnets 181 are magnetic materials that become at least partially demagnetized at temperatures above the normal operating temperature of the surgical drill system 60 (such as at room temperature in an operating room) but below the temperature at which the drill bits 66 are cleaned and sanitized after usage, such as through autoclaving, such as at or above 80 degrees Celsius.

The demagnetization of the magnets 181 in the drill bit assembly 65 functions to alter, or eliminate, the generated magnetic field of a particular strength and direction that is used to identify the respective coupled drill bit assembly 65. In this manner, the operator can have a reasonable level of assurance that the coupled drill bit assembly 65, which has been identified based upon the identified magnetic field signal, has not previously been heated to a temperature above the demagnetization temperature, such as during a cleaning and sanitizing process after a first use.

Conversely, if the drill bit assembly 65 cannot be identified on the basis of the identified generated magnetic field, the operator can reasonably conclude that the coupled drill bit assembly 65 has either been heated to temperatures above the demagnetization temperature (which may be indicative of previous use, cleaning and sanitization as described above), or is a drill bit assembly that does not include an identification feature as provided herein.

Figure 7A:
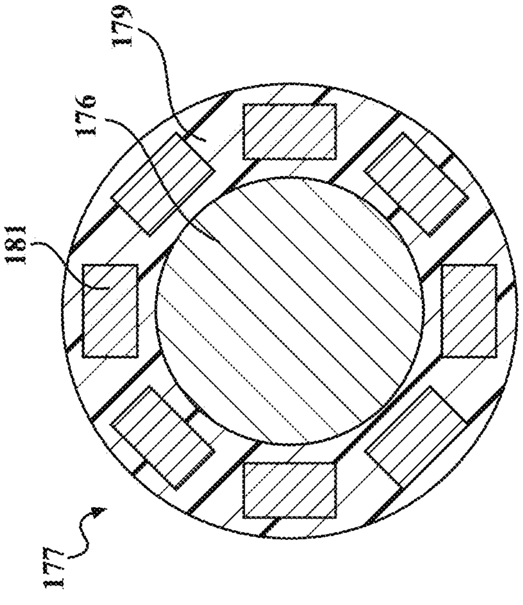
FIG. 7A is a section view of the drill bit assembly of FIG. 7 taken along line 7A-7A in accordance with one configuration.

When a sleeve configuration is utilized, and as best illustrated in the sectional views of FIGS. 7A and 7B, the sleeve 179 may be secured to, or otherwise at least partially surround, a portion of the shank 176 between the proximal end 178 and the distal end 180. Accordingly, the sleeve 179, and the magnets 181 coupled to the sleeve 179, rotate as the coupled drill bit 66 rotates during usage.

The sleeve 179, similar to the bearing region 184 of the drill bit 66, may be sized so as to be received within and rotate relative to the measurement cannula 134 of the measurement module 128. Accordingly, the thickness of the sleeve 179, extending radially from the shank 176, is designed to be as thin as practical and fit within an inner lumen of the measurement cannula 134. Accordingly, the outer surface of the sleeve 179 may not rub against an inner surface of the measurement cannula 134 during use.

The outer surface of the sleeve 179 may be designed to extend at a constant radial thickness around the shank 176 so as not to affect the rotation of the drill bit 66 during usage. The sleeve 179, as shown in FIGS. 7, 7A and 7B, may comprise a material that does not interfere with the magnetic field generated by the one or more magnets 181, alternatively referred to herein as a non-magnetic material. In certain configurations, the sleeve 179 comprises a polymer. In some configurations, the polymer may have a melting point or a glass transition temperature above the normal operating temperature of the surgical drill system 60 (such as at room temperature in an operating room) but below the temperature at which the drill bits 66 are autoclaved after usage, such as at or above 120 degrees Celsius. In other configurations, the polymer may have a melting point or a glass transition temperature that is at or above 130 degrees Celsius. In further configurations, the polymer may have a melting point or a glass transition temperature at or above 140 degrees Celsius. In still further configurations, the polymer may have a melting point or a glass transition temperature at or above 150 degrees Celsius. Even still further, the polymer may comprise a durable, relatively hard plastic material. It is also contemplated that the sleeve 179 may be formed from other materials that have a melting point above the normal operating temperature of the surgical drill system 60 (such as at room temperature in an operating room) but below the temperature at which the drill bits 66 are autoclaved after usage, such as at or above 120 degrees Celsius.

In another configuration of the drill bit assembly 65 comprising a sleeve 179 shown in FIGS. 13-16, the sleeve 179 may comprise non-magnetic material and magnetic material being dispersed in the non-magnetic material. The magnetic material may be uniformly dispersed in the non-magnetic material such that no portion of the sleeve 179 is more heavily concentrated with magnetic material than other portions. The identification feature in this configuration is the magnetic material in of the sleeve 179. The magnetic material may be programmed (i.e. calibrated) in a manner that identifies a configuration of the cutting tip portion 70 of the drill bit 66. The magnetic material may comprise flakes, fragments, and/or solid particles. The magnetic material may comprise a neodymium magnet and or a samarium-cobalt magnet. In other configurations the magnetic material comprises iron. Other magnetic materials are contemplated.

Figure 13:
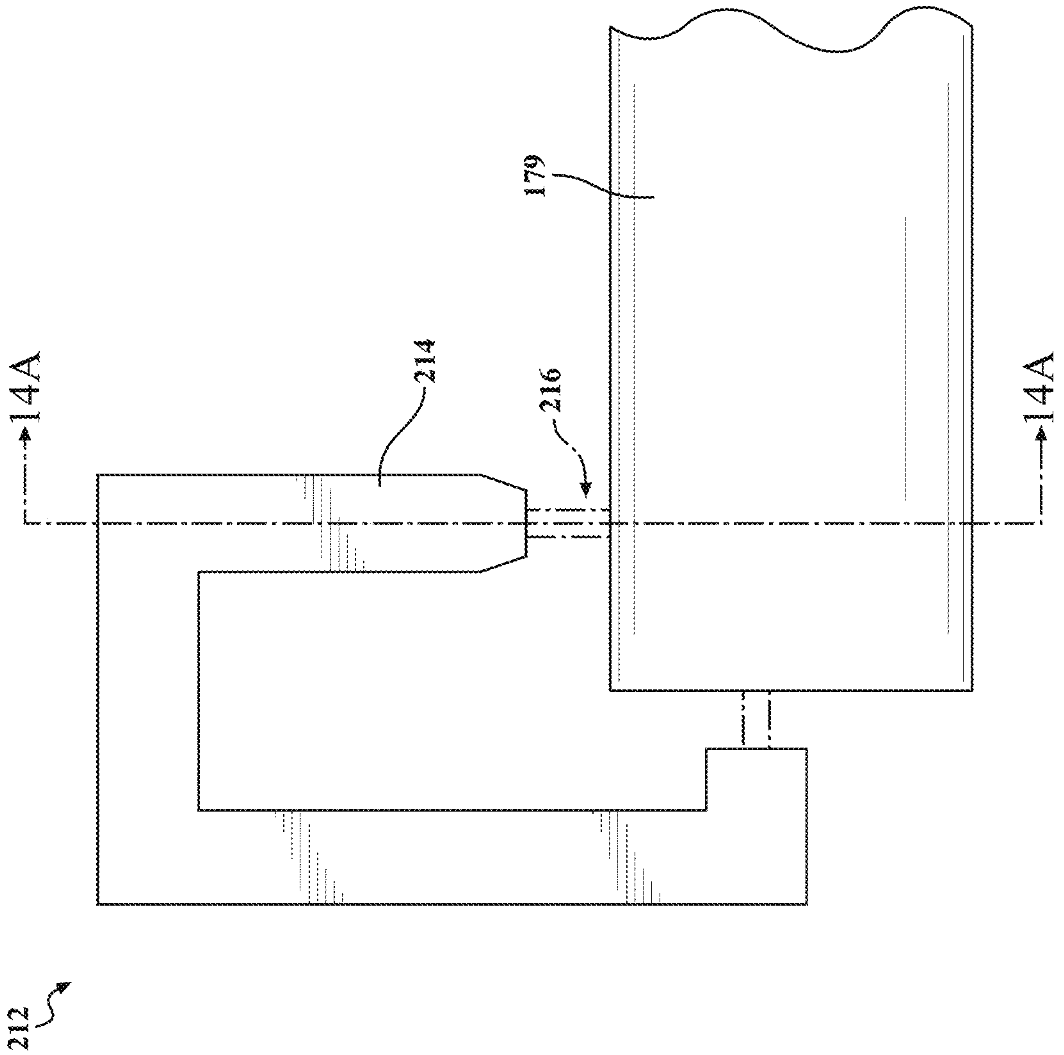
FIG. 13 is an elevation view of a programming fixture and a sleeve of the drill bit assembly.
Figure 14B:
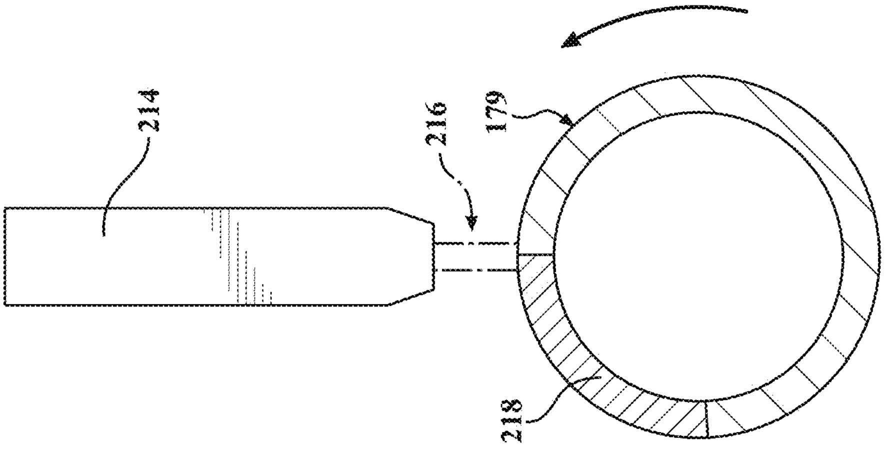
FIG. 14B is a section view of the pole piece and sleeve of FIG. 14A with the sleeve in a second orientation.
Figure 14A:
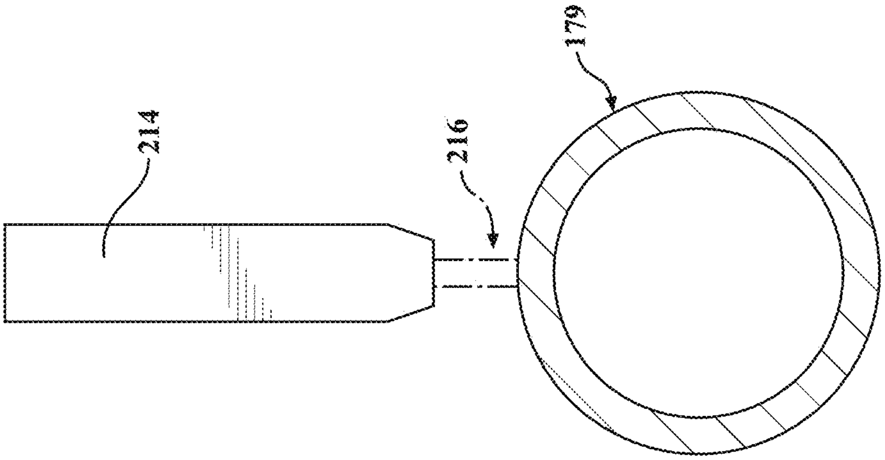
FIG. 14A is section view of a pole piece of the programming fixture and the sleeve of FIG. 13 taken along lines 14A-14A with the sleeve in a first orientation.
Figure 14C:
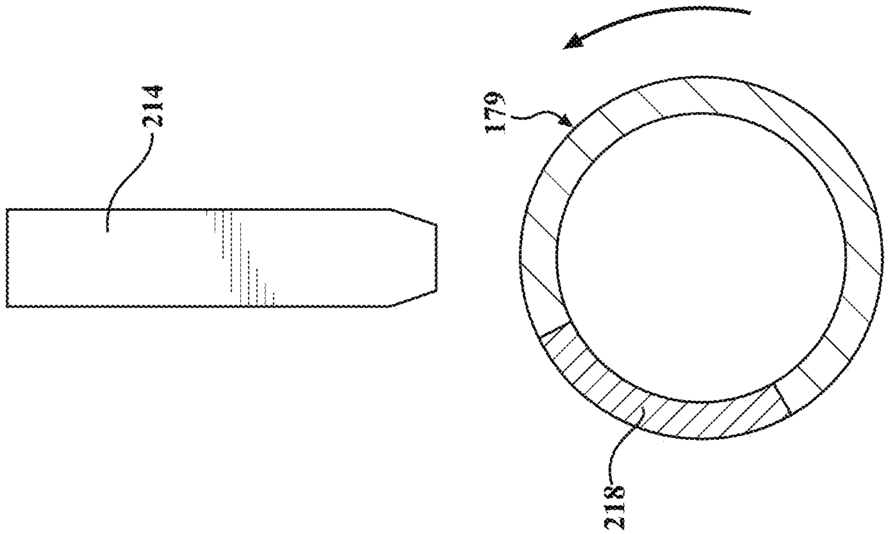
FIG. 14C is a section view of the pole piece and sleeve of FIGS. 14A and 14B with the sleeve in a third orientation.
Figure 14D:
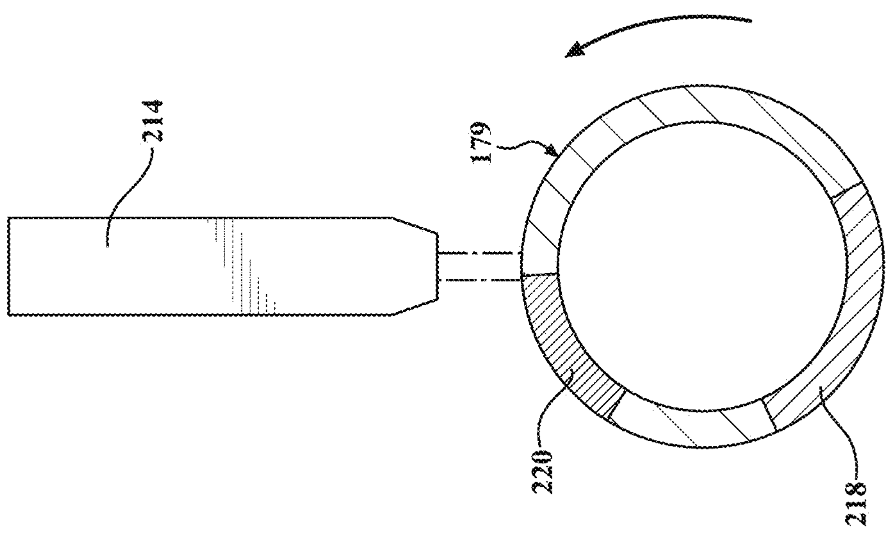
FIG. 14D is a section view of the pole piece and sleeve of FIGS. 14A-14D with the sleeve in a fourth orientation.

An exemplary configuration for programming such a sleeve 179 is shown in FIGS. 13-14D. FIG. 13 illustrates a programming fixture 212 that includes a pole piece 214 for focusing a magnetic field 216 at certain locations of the sleeve 179. In FIG. 14A, the pole piece 214 begins to focus a magnetic field 216 having a first polarity on the sleeve 179. In FIG. 14B the sleeve has rotated relative to the pole piece 214 a certain number of degrees while the pole piece 214 focused the magnetic field 216 with the first polarity. As such, the magnetic material that was subjected to the magnetic field will now emit a magnetic field with the first polarity for a certain arc length 218. At this point the magnetic field 216 from the pole piece 214 has been turned off and the sleeve 179 continues rotating relative the pole piece 214 to the orientation shown in FIG. 14C. In FIG. 14C, a certain arc length of the sleeve 179 has neutral polarity and does not emit a magnetic field as the magnetic field 216 from the pole piece 214 was not operating. Then the magnetic field 216 is applied with a second polarity opposite the first polarity for a certain arc length 220 shown in FIG. 14D. FIG. 14D illustrates one configuration of a programmed sleeve that has different arc lengths and polarity about the axis. When the sleeve 179 is coupled to the drill bit 66 and rotated about an axis, the sensor may comprise a magnetoresistance sensor to generate signals responsive to a varying magnetic field created by the now programmed and selectively magnetized sleeve 179. The Figures illustrated in FIGS. 14A-14D illustrate one configuration of a magnetic programming sequence. It is contemplated that other magnetic programming sequences may change programming parameter such as a pulse frequency of magnetic field application on the sleeve 179, a phase offset or angular offset of the spacing between arc lengths of magnetized portions and unmagnetized portions of the sleeve 179, a strength of the magnetic field (which may be increased or decreased by saturating a portion of the magnetic material of the sleeve 179 with more or less of the magnetic field from the pole piece 214), speed of rotation of the sleeve 179 while rotating relative the pole piece 214, the polarity of the magnetic field, and/or combinations thereof. While the sleeves 179 shown in FIGS. 14A-14D do not include a drill bit 66 coupled to them during the selective programming, it is contemplated that the drill bit 66 may be coupled to the sleeve 179 during some types of programming. Further, while the programming process described above includes the step of rotating the sleeve 179 relative to the pole piece 214, it is contemplated that selective programming of the sleeve 179 may be accomplished in other manners by facilitated relative movement between the pole piece 214 and the sleeve 179. The programmed sleeve 179 may be coupled to the shank 176 of the drill bit through interference fit, molding, fasteners, adhesives, or otherwise.

As shown in FIG. 14D the shape of the magnetic field may be asymmetrical about the axis of the sleeve 179. The sleeve 179 may be divided into four quadrants about the axis, a first quadrant, a second quadrant, a third quadrant, and a fourth quadrant. A magnetic field generated by the first quadrant may be different from the second quadrant, the third quadrant, and/or the fourth quadrant in terms of size, strength, polarity, or combinations thereof. The shape of the magnetic field of the sleeve 179 may also be asymmetrical along the axis of the shank 176.

One benefit of programming sleeves is that a drill bit system with two or more sleeves could be manufactured identically reducing the number of different types of parts and the machines to produce them. Two or more sleeves 179 may be identical until programming. After programming, each sleeve 179 may emit a unique sleeve associated with a certain configuration of a cutting tip portion 70 or shank 176. Similar to other configurations described herein, the cutting configurations of different cutting tip portions 70 of distinct drill bits 66 may be selected from a length of the drill bit 66, a material of the drill bit 66, a diameter of a distal end 180 of the shank 176 of the drill bit 66, a cross-sectional area of the drill bit 66, a type of drill bit 66, a rake angle of the drill bit 66, a flute angle of the drill bit 66, and/or a point angle of the drill bit 66.

Figure 15:
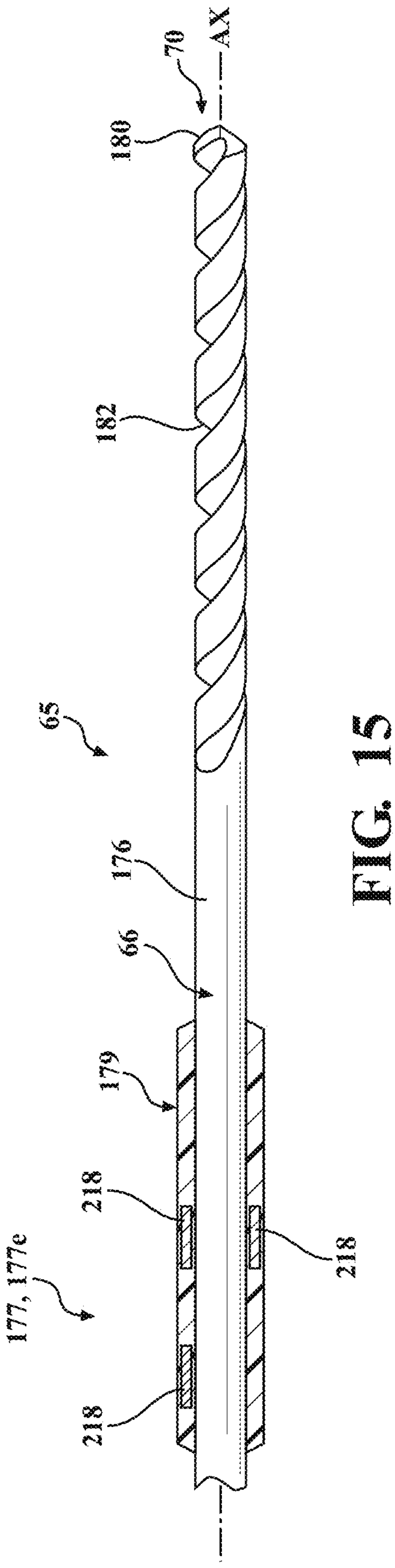
FIG. 15 is an elevation view of a configuration of the drill bit assembly including a drill bit and multiple arrays of magnetic material coupled to one sleeve.

As shown in FIG. 15, the sleeve 179 may comprise two configurations of the programmed magnetic material of the sleeve 179 may comprise a first array of magnets disposed circumferentially about the shank 176. Another configuration of may be programmed differently than the first array. The second array of magnets disposed circumferentially about the shank and may be disposed axially spaced from the first array of magnets. The first programming of the first configuration of magnetic material emits a first magnetic field. The second programming of the second configuration of magnetic material emits a second magnetic field different from the first magnetic field.

Figure 16:
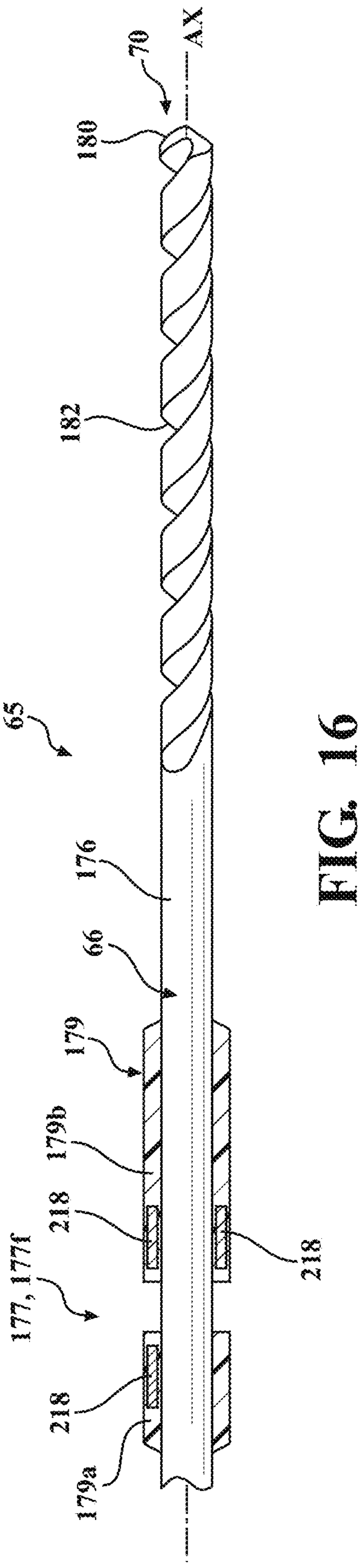
FIG. 16 is an elevation view of a configuration of the drill bit assembly including a drill bit having an array of magnetic material coupled to each of two sleeves.

In another configuration shown in FIG. 16, two different programmed arrays of magnetic material are shown. In this configuration, the sleeve 179 is split into a proximal sleeve portion **179*a* and a distal sleeve portion 179*b*. This is another way to use multiple programmed arrays of magnetic material without having to put multiple programmed arrays on a single sleeve 179. It is contemplated that the drill bit assembly 65 may include three or more sleeve portions 179*a*, 179*b***.

As with other configurations of the sleeve 179, the non-magnetic material of the sleeve 179 may have a glass transition temperature or a melting temperature at or below 120 degrees Celsius. The magnetic material may become at least partially demagnetized when heated to a temperature at or above 80 degrees Celsius.

As noted above, the sleeve 179 may comprise a material having a melting point or a glass transition temperature below the temperature at which the drill bits 66 are autoclaved. As such, the material forming the sleeve 179 may be configured to melt and/or deform when exposed to temperatures greater than the melting point or the glass transition temperature, such as during an autoclaving or cleaning/sanitizing process at elevated temperatures. The melting and deforming of the sleeve material can be designed therefore to alter the relative location of the magnets 181 within the sleeve 179 after melting or deformation. This in turn may alter the magnetic field generated by the magnets 181 which are coupled within the sleeve 179, which may prevent the drill bit 66 of the drill bit assembly 65 from being identified. In case that optical identification features are used on the sleeve, similarly, the melting and deforming of the sleeve material can be designed to alter the appearance of the optical features after melting or deformation. For instance, if a label were used, deformation of the sleeve 179 to which the label is attached may result in the label being damaged or deformed to prevent identification. In another example, the label may comprise a heat-sensitive label that is configured to deform on its own during the autoclaving process or when exposed to temperatures at or above 120 degrees Celsius.

Similar to the demagnetization of the magnets 181 as described above, the melting and deforming of the sleeve 179 in the drill bit assembly 65, may result in subsequent movement of the location of the magnets 181, functions to alter, or potentially eliminate, the generated magnetic field of a particular strength and direction of the coupled magnets 181 that is used to identify the coupled drill bit 66, even when such magnets 181 are not demagnetized when the sleeve 179 is melted or deformed. In this manner, the operator can have a reasonable level of assurance that the coupled drill bit assembly 65, which has been identified based upon the identified magnetic field signal, has not previously been heated to a temperature above the melting temperature of the sleeve material, such as during a cleaning and sanitizing process after a first use. Conversely, if the drill bit assembly 65 is not identified on the basis of the generated magnetic field, the operator can reasonably conclude that the coupled drill bit assembly 65 has either been heated to temperatures above the melting temperature of the sleeve material (which may be indicative of previous use, cleaning and sanitization as described above), or is not a drill bit assembly 65 having an identification feature as described herein.

In certain instances, where the drill bit assembly 65 is heated to a particular temperature that is above both the demagnetization temperature of the magnet 181 and above the melting temperature of the sleeve material of the sleeve 179, the generated magnetic field of the magnets 181 may be altered by both the demagnetization of the magnets 181 and the altering of location of the magnets 181 resulting from the melting and deformation of the sleeve material of the sleeve 179.

The sleeve 179 may be coupled to the drill bit 66 in many ways. In one configuration, the sleeve 179 may be slid over the proximal end 178 or distal end 180 of the drill bit 66 and interference fit around the exterior surface of the shank 176 at a desired location. In this configuration, the sleeve 179 may be pre-formed with the embedded magnets 181 (such as in FIG. 6A, 11A, or 12A), or the magnets 181 may be secured to the outer surface of the sleeve 179 with an adhesive or a fastener (not shown) after installation. In this configuration, an adhesive (not shown) may be introduced between the sleeve 179 and the shank 176 to secure the sleeve 179 to the shank 176.

Still further, the sleeve 179 may be over-molded onto the drill bit 66 at the desired location. In one configuration, the magnets 181 are introduced into a mold, along with the drill bit 66, and the polymer for forming the sleeve 179 is introduced within the cavity portion of the mold between the drill bit 66 and magnets 181 to form the sleeve 179 having embedded magnets 181 such as illustrated in FIG. 7A.

Alternatively, the drill bit 66 alone may be introduced within the mold, and the polymer for forming the sleeve 179 is introduced within the cavity portion of the mold around the drill bit 66. The resultant structure is removed from the mold, and the magnets 181 may be secured to the outer surface of the sleeve 179 with an adhesive or a fastener (not shown) or through interference fit after the molding step.

Referring back to FIGS. 1-5, in the representative configuration illustrated herein, the handpiece 62 is realized as a handheld drill with a pistol-grip shaped handpiece body 74 which releasably attaches to a battery 76 (battery attachment not shown in detail). However, it is contemplated that the handpiece body 74 can have any suitable shape with or without a pistol grip. While the illustrated handpiece 62 employs a battery 76 which is releasably attachable to the handpiece body 74 to provide power to the handpiece 62 utilized to rotate the drill bit 66, it will be appreciated that the handpiece 62 may be configured in other ways, such as with an internal (e.g., non-removable) battery, or with a tethered connection to an external console, power supply, and the like. Other configurations are contemplated.

Figure 3:
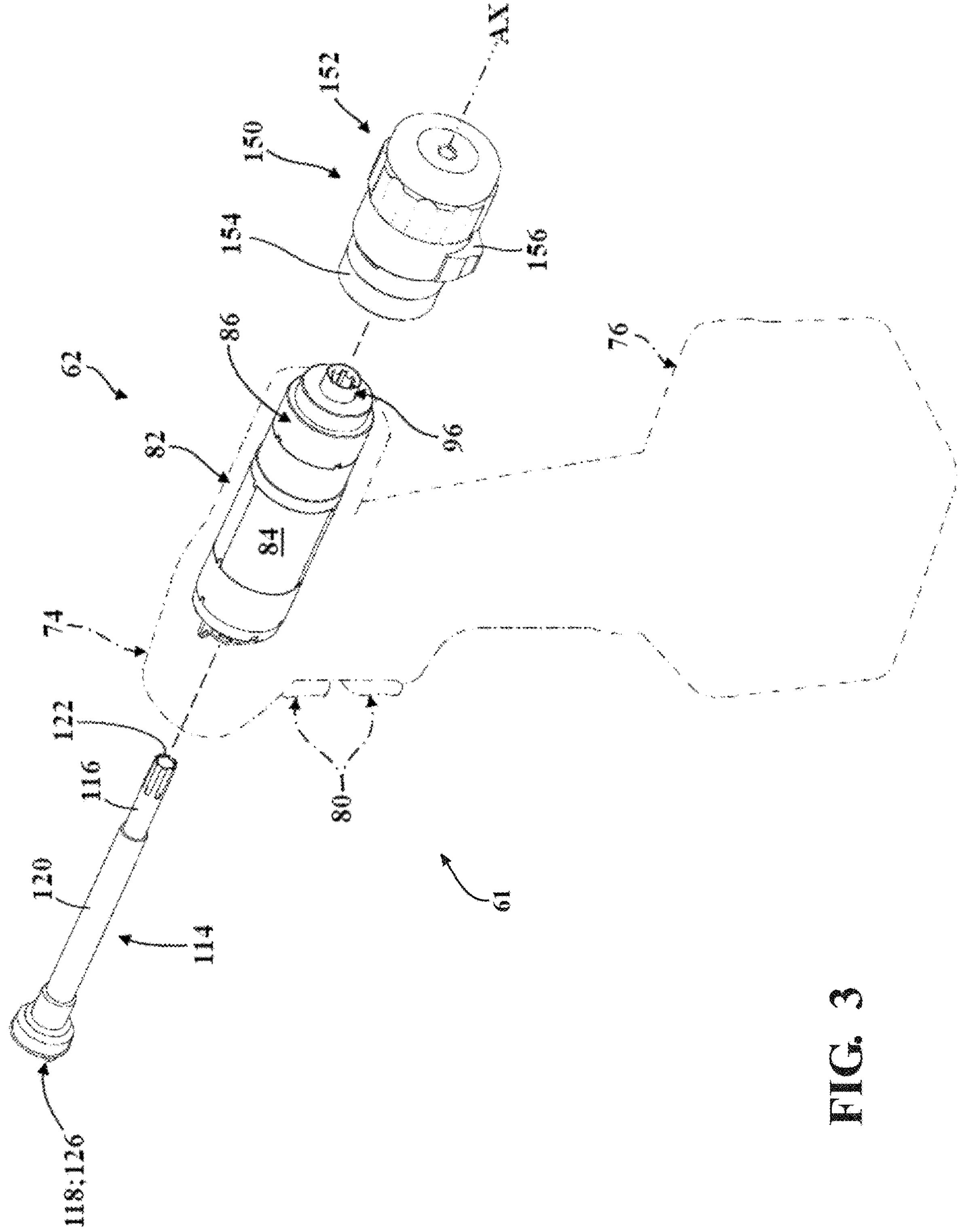
FIG. 3 is a partially-exploded perspective view of portions of the surgical instrument of FIGS. 1-2, shown with the drive assembly and the release mechanism spaced from a phantom outline of the handpiece body to depict an actuator assembly.

In the illustrated configuration, the battery 76 or other power source provides power to a controller 78 (depicted schematically in FIG. 5) which, in turn, is disposed in communication with an input control 80 and an actuator assembly 82 (see also FIG. 3). The input control 80 and the actuator assembly 82 are each supported by the handpiece body 74. The controller 78 is generally configured to facilitate operation of the actuator assembly 82 in response to actuation of the input control 80. The input control 80 has a trigger-style configuration in the illustrated configuration, is responsive to actuation by a user (e.g., a surgeon), and communicates with the controller 78, such as via electrical signals produced by magnets (other than the magnets 181 described above) and Hall effect sensors. Thus, when the operator actuates the input control 80 to operate the handpiece 62, the controller 78 directs power from the battery 76 to the actuator assembly 82 which, in turn, generates rotational torque employed to rotate the drill bit 66, as described in greater detail below. The handpiece body 74, the battery 76, the controller 78, and the input control 80 could each be configured in a number of different ways to facilitate generating rotational torque without departing from the scope of the present disclosure.

Figure 5:
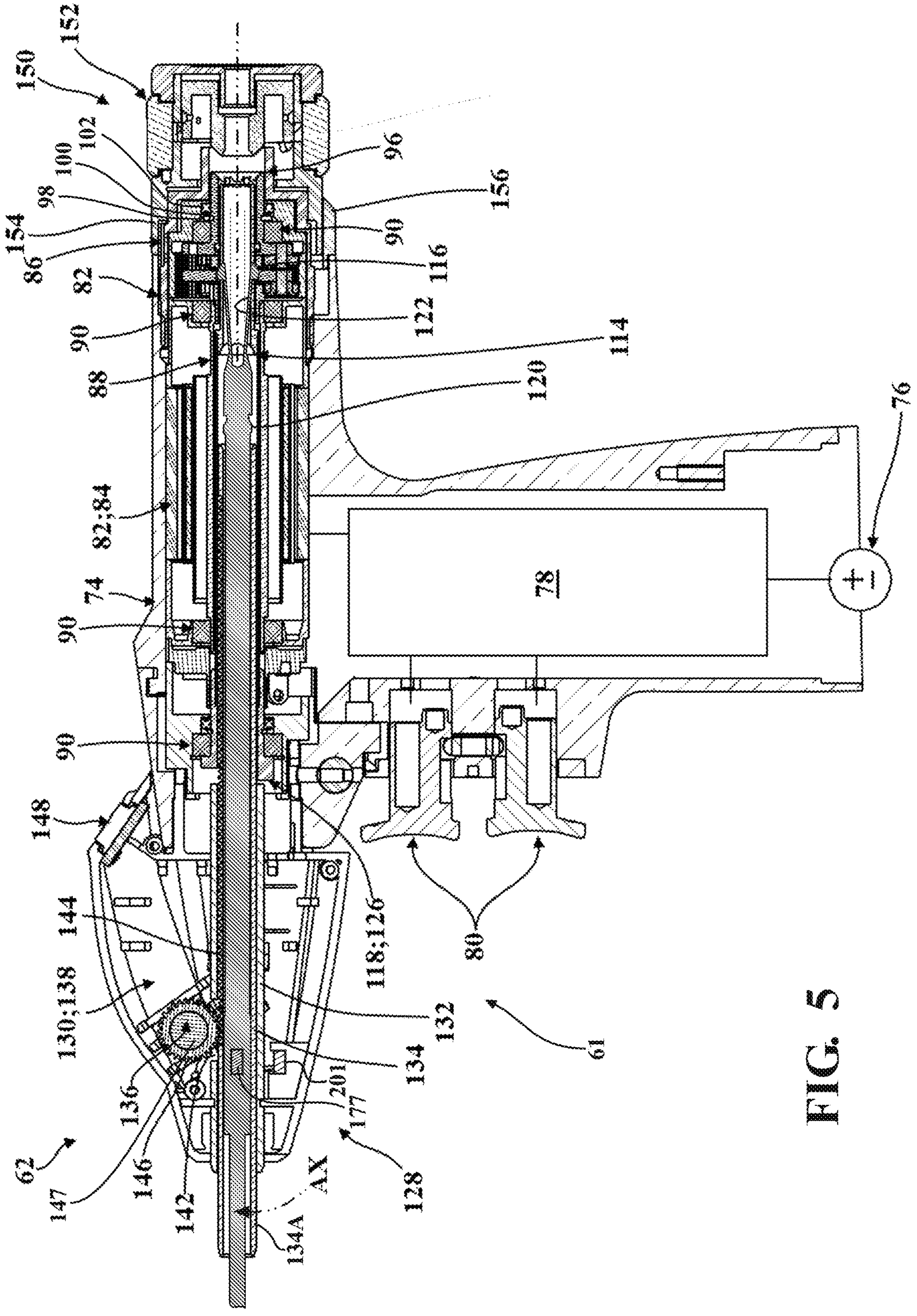
FIG. 5 is a sectional view taken longitudinally through the surgical instrument of FIGS. 1-4 illustrating the arrangement of the identification feature and the sensor located within the measurement module.

As also shown in FIG. 3, the actuator assembly 82 may comprise an electric motor 84 and a gearset 86 which are each supported within the handpiece body 74. The motor 84 is configured to selectively generate rotational torque in response to commands, signals, and the like received from the controller 78. As is best shown in FIG. 5, the motor 84 comprises a rotor cannula 88 supported for rotation about the axis AX by a pair of bearings 90. A drive gear arranged adjacent to the gearset 86 is coupled to and rotates concurrently with the rotor cannula 88, and is employed to transmit rotational torque to the gearset 86. To this end, in the illustrated configuration, the gearset 86 is realized as two-stage compound planetary arrangement and generally comprises a ring gear housing 94 which, among other things, rotationally supports an output hub 96 via a bearing 90, as well as one or more retaining clips 98, washers 100, and/or seals 102. However, other configurations of the gearset 86 are contemplated.

Further details of one configuration of a gearset 86 are described, for example, in U.S. patent application Ser. No. 15/887,507, filed on Feb. 2, 2018 and entitled "Drill Bit for Handheld Surgical Instrument, the contents of which are herein incorporated by reference in their entirety, and describe wherein the rotation of the drive gear via actuation of the motor 84 effects concurrent rotation of the output hub 96, and wherein the output hub 96 rotates concurrently with the drill bit 66. The actuator assembly 82 could be configured in other ways without departing from the scope of the present disclosure. By way of non-limiting example, while the illustrated actuator assembly 82 employs a compound planetary arrangement to adjust rotational speed and torque between the drive gear of the motor 84 and the output hub 96, other types of gearsets 86 could be utilized in some configurations. Moreover, while the illustrated actuator assembly 82 employs an electrically-powered brushless DC motor to generate rotational torque, other types of prime movers could be utilized. Other configurations are contemplated.

As noted above, rotational torque generated by the motor 84 effects rotation of the output hub 96 which, in turn, rotates concurrently with the coupled drill bit 66. To this end, and as is best shown in FIGS. 2-5, the handpiece 62 further comprises a drive assembly 114 which generally extends through the various cannulated components of the actuator assembly 82 into splined engagement with the output hub 96 of the gearset 86. The drive assembly 114 is configured to facilitate releasable attachment between the drill bit 66 and the handpiece 62. The drive assembly 114 generally comprises a driving cannula 116, a driving head 118, and a driving body 120 which extends between, and rotates concurrently with, the driving cannula 116 and the driving head 118. The drive assembly 114 is supported for rotation about the axis AX within the handpiece body 74 via splined engagement with the output hub 96 adjacent the driving cannula 116, and via an arrangement of bearings, washers, and seals adjacent the driving head 118. It is contemplated that the drill bit 66 may be configured to attach to the handpiece 62 to receive torque in a manner different from that described above.

Further details of the drive assembly 114 are also described, for example, in U.S. patent application Ser. No. 15/887,507, the contents of which are also herein incorporated by reference in their entirety. In the illustrated configuration, the driving head 118 of the drive assembly 114 comprises a coupling, generally indicated at 126, which is provided to facilitate transmitting rotational torque when the handpiece 62 is utilized in connection with other applications besides rotating the drill bit 66 of the present disclosure. More specifically, the illustrated drive assembly 114 is configured such that the handpiece 62 can rotate, drive, or otherwise actuate a number of different types of surgical instruments, tools, modules, end effectors, and the like, which can be configured to engage and rotate concurrently with either the bore 122 of the driving cannula 116, or the coupling 126 of the driving head 118. It will be appreciated that this configuration allows the same handpiece 62 to be utilized in a broad number of medical and/or surgical procedures. However, it is contemplated that the drive assembly 114 could be configured differently in some configurations, such as to omit a driving head 118 with a coupling 126 in configurations where the handpiece 62 configured for dedicated use with the drill bit 66 of the present disclosure.

Referring back to FIGS. 1-3, the illustrated configuration of the handpiece 62 further comprises a release mechanism, or coupling mechanism, generally indicated at 150, configured to facilitate removal of the drill bit 66. The coupling mechanism 150 generally comprises a release subassembly 152, a keeper body 154, and a housing adapter 156. The keeper body 154 and the housing adapter 156 are respectively configured to secure the release subassembly 152 to the actuator assembly 82 and the handpiece body 74, and could be realized with a number of different configurations or could be integrated into other parts of the handpiece 62 in some configurations.

As noted above, the drill bit 66 generally extends along the axis AX between the cutting tip portion 70 and the insertion portion 72, and is configured for releasable attachment to the handpiece 62 described herein and illustrated throughout the drawings via engagement between the interface 124 of the drill bit 66 and the bore 122 of the driving cannula 116 of the drive assembly 114. The driving cannula 116, in turn, cooperates with the output hub 96 of the gearset 86 of the actuator assembly 82 to facilitate rotating the drill bit 66 about the axis AX.

Figure 4:
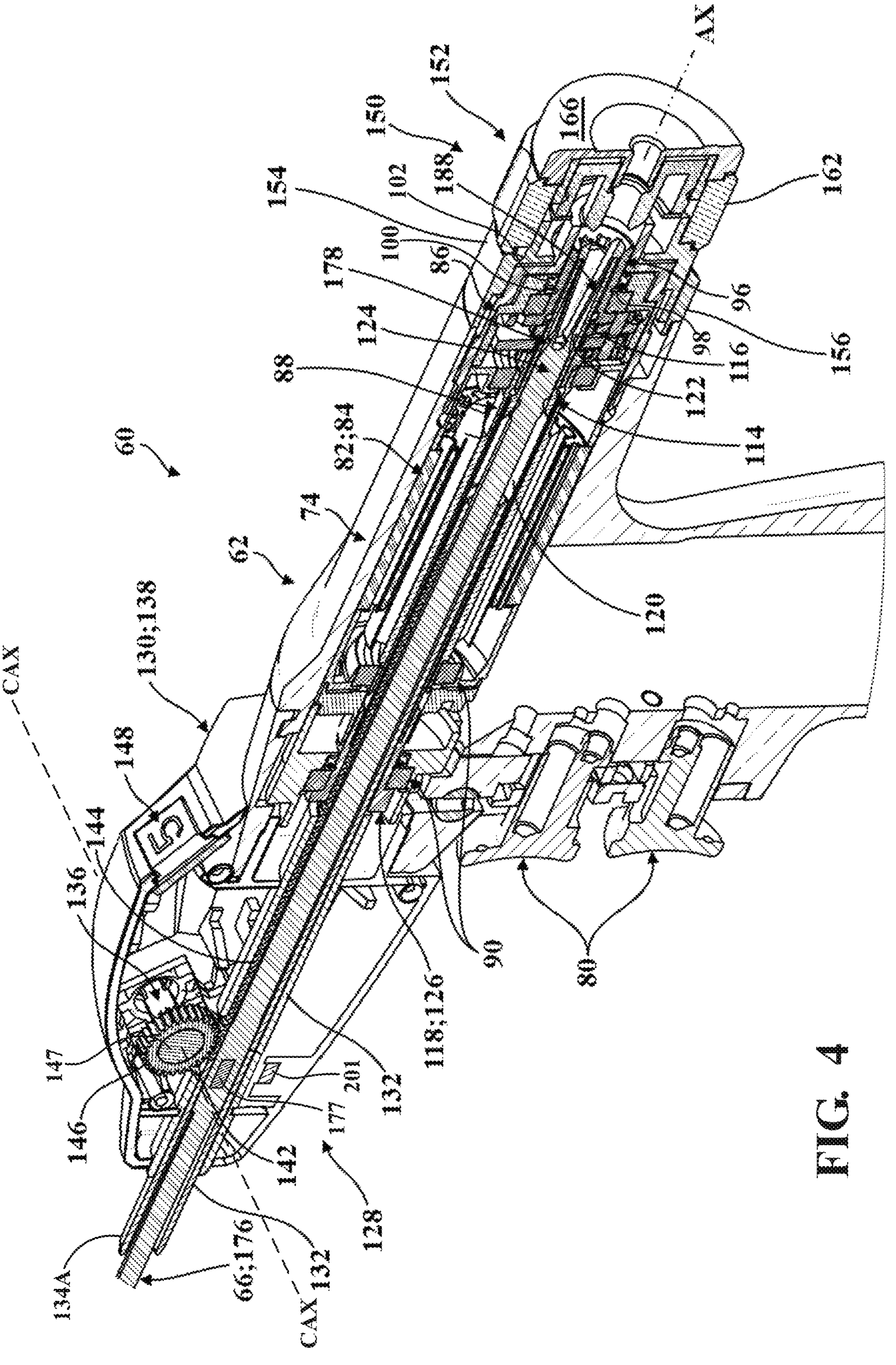
FIG. 4 is a partial isometric sectional view taken along line 4-4 in FIG. 1 illustrating the arrangement of the identification feature and the sensor located within the measurement module.

The illustrated configuration of the surgical drill system 60 further comprises the measurement module (alternatively referred to sometimes as a measurement head), generally indicated at 128, which may be configured to releasably attach to the handpiece 62 to provide the surgeon with measurement functionality during use. To this end, and as is best shown in FIGS. 4 and 5, the measurement module 128 may generally comprise a housing 130, a guide bushing 132, and a measurement cannula 134 (i.e., a measurement probe, or depth measurement extension), which includes a distal end 134A adapted for placement against a workpiece 62, or tissue. Suitable examples of a measurement module are described in PCT/IB2018/056251, which is hereby incorporated by reference in its entirety. The housing 130 may be releasably attachable to the handpiece 62 and generally support the various components of the measurement module 128. The illustrated housing 130 may be formed as a pair of housing components 138 which interlock or otherwise attach together, and may be configured for disassembly to facilitate cleaning or servicing the measurement module 128. It should be appreciated that the measurement module 128 may be formed as an integral component of the handpiece 62, or may be in the form of a component that is affixed or otherwise secured to the handpiece 62 in a manner wherein the measurement module 128 is not removable from the handpiece 62 after use.

In the illustrated configuration, the housing components 138 and the guide bushing 132 comprise correspondingly-shaped features arranged to prevent relative axial and rotational movement therebetween, such as via notches formed in the guide bushing 132 which fit into webs or ribs formed in the housing components (not shown in detail). The guide bushing 132 may further comprises a window 142 as described in detail below.

The measurement cannula 134 may be disposed within the guide bushing 132 and is supported for translational movement along the axis AX relative to the handpiece 62. An elongated recessed slot 143 (partially depicted in FIG. 2) may be formed transversely into the measurement cannula 134 and extends longitudinally. While not specifically illustrated herein, the elongated recessed slot 143 may be shaped and arranged to receive a travel stop element which, in turn, is supported by the housing 130 and likewise extends through an aperture formed transversely through the side of the guide bushing 132. This arrangement may serve to limit how far the measurement cannula 134 may be axially extended or retracted relative to the guide bushing 132 and housing 130, and may also prevent the measurement cannula 134 from rotating about the axis AX. However, it will be appreciated that the measurement module 128 could be configured to limit or prevent movement of the measurement cannula 134 in other ways without departing from the scope of the present disclosure.

As illustrated, the measurement cannula 134 further comprises rack teeth 144 which are disposed in meshed engagement with a gear 146 of a transducer assembly 136. As shown in FIG. 5, the window 142 of the guide bushing 132 is arranged adjacent to the transducer assembly 136 to facilitate the meshed engagement between the rack teeth 144 and the gear 146. The gear 146 includes a shaft portion 147 extending along a common gear axis CAX. The gear 146 itself is rotatable 360 degrees about the common gear axis CAX as the probe 134 moves along the axis AX relative to the housing 130.

The transducer assembly 136 is responsive to rotation of the gear 146 resulting from axial movement of the measurement probe 134 in order to generate electrical signals (i.e., a transducer signal) representing changes in the position of the measurement probe 134 relative to the housing 130 along the axis AX, which correspond to the relative positioning of the distal end 134A of the measurement cannula 134 relative to the housing 130 when the surgical drill 61 is placed against the workpiece. Thus, it will be appreciated that the transducer assembly 136 is able to provide the surgical instrument 62 with enhanced functionality. By way of example, in some configurations, the transducer assembly 136 may be disposed in communication with the controller 78, which may be configured to interrupt or adjust how the motor 84 is driven based on movement of the measurement probe 134, such as to slow rotation of the drill bit 66 at a specific drilling depth into the workpiece. The transducer assembly 136 may also be disposed in communication with an output device 148, such as a display screen, one or more light-emitting diodes (LEDs), and the like, to provide the surgeon with information relating to movement of the measurement probe 134, such as to display a real-time drilling depth, a recorded historical maximum drilling depth, and the like. Other configurations are contemplated. The output device 148 may be part of the measurement module that is removable. Further, while the transducer assembly 136 and measurement cannula 134 illustrated in FIG. 4 collectively comprise a rack and pinion design with the rack teeth 144 of the measurement cannula 134 and the gear 146 of the transducer assembly 136, it is contemplated that the transducer assembly 136 may comprise one or more sensors such as a potentiometer, an optical sensor, and a linear variable displacement transformer to generate transducer signals responsive to displacement of the measurement cannula 134 relative to the housing 130.

The measurement cannula 134 and the guide bushing 132 may be formed of a variety of materials, preferably materials that do not alter the signal/magnetic field signature generated by the identification feature 177/one or more magnets 181, such as non-magnetic materials as described above. Exemplary non-magnetic materials for use in forming the measurement cannula 134 and the guide bushing 132 include certain polymers that can be molded or otherwise formed into hard, durable desired shape. In one configuration, the polymer comprises a hard plastic material.

As shown in FIGS. 4 and 5, the surgical drill system 60 also includes a sensor 201 that is configured for generating one or more signals (e.g., an identification signal) responsive to the identification feature 177. For example, the sensor 201 may be configured to generate the identification signal responsive to a magnetic field or magnetoresistance generated from the one or more magnets 181, of the coupled drill bit assembly 65 as the drill bit assembly 65 rotates about the axis AX during operation of the surgical drill system 60. In particular, as shown in FIGS. 4 and 5, the sensor 201 is configured to generate the identification signal responsive to the identification feature 177, such as the magnetic field or magnetoresistance generated from the one or more magnets 181 (i.e., is a magnetic field sensor or a hall effect sensor), coupled to the respective coupled drill bit 66. The sensor 201 may generate the identification signal even when the measurement cannula 134 is disposed between the sensor 201 and the identification feature 177 when the drill bit assembly 65 is rotating about the axis AX. The identification signal generated by the sensor 201 corresponds to the received generated signal/magnetic field on the respective drill bit 66 that is coupled to the handpiece 62. The controller 78 is configured to receive and interpret the identification signal, or to receive and interpret the magnetic field signature signal, to identify the coupled drill bit 66 of the drill bit assembly 65.

The sensor 201 is preferably positioned relative to the identification feature 177, such as one or more magnets 181, such that it can receive the generated signal/magnetic field when the respective drill bit 66 is properly coupled to the handpiece 62 and is rotating about the axis AX (such as when the operator is depressing the input control 80). In particular, the sensor 201 may be positioned such that it receives the generated signal/magnetic field through the measurement cannula 134 and optionally through the guide bushing 132 as the drill bit assembly 65 is rotating about the axis AX.

In one configuration, the sensor 201 may be coupled to or positioned within the measurement module 128, and in particular coupled to or positioned within the housing 130 of the measurement module 128, in a position in proximity to the identification feature 177 such as one or more magnets 181 when the drill bit assembly 65 is properly coupled to the handpiece 62.

Figure 10A:
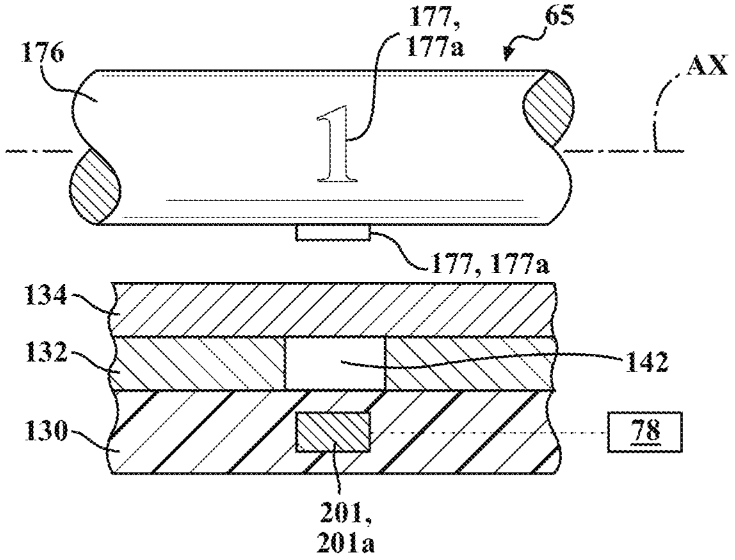
FIG. 10A is a partial schematic view of the drill bit, identification feature, guide bushing, measurement cannula, and sensor of FIGS. 4 and 5.

Even more particularly, as illustrated in one configuration in FIGS. 4 and 5, the sensor 201 may be positioned within the housing 130 opposite to or offset from the gear 146 of the transducer assembly 136 relative to the drill bit assembly 65 in a direction normal to the axis AX. In such configurations, the sensor 201 may be aligned with the window 142 of the guide bushing 132 in a direction normal to the axis AX. Accordingly, the sensor 201 receives the generated signal/magnetic field signal from the identification feature 177, such one or more magnets 181 or optical features through the measurement cannula 134 and through the window 142 of the guide bushing 132 as the drill bit assembly 65 rotates about the axis AX, as best shown in FIG. 10A.

However, in other configurations, the sensor 201 may be positioned in other stationary portions of the surgical drill system 60 that are capable of receiving the generated signal/magnetic field signal from the identification feature 177/one or more magnets 181.

Figure 8:
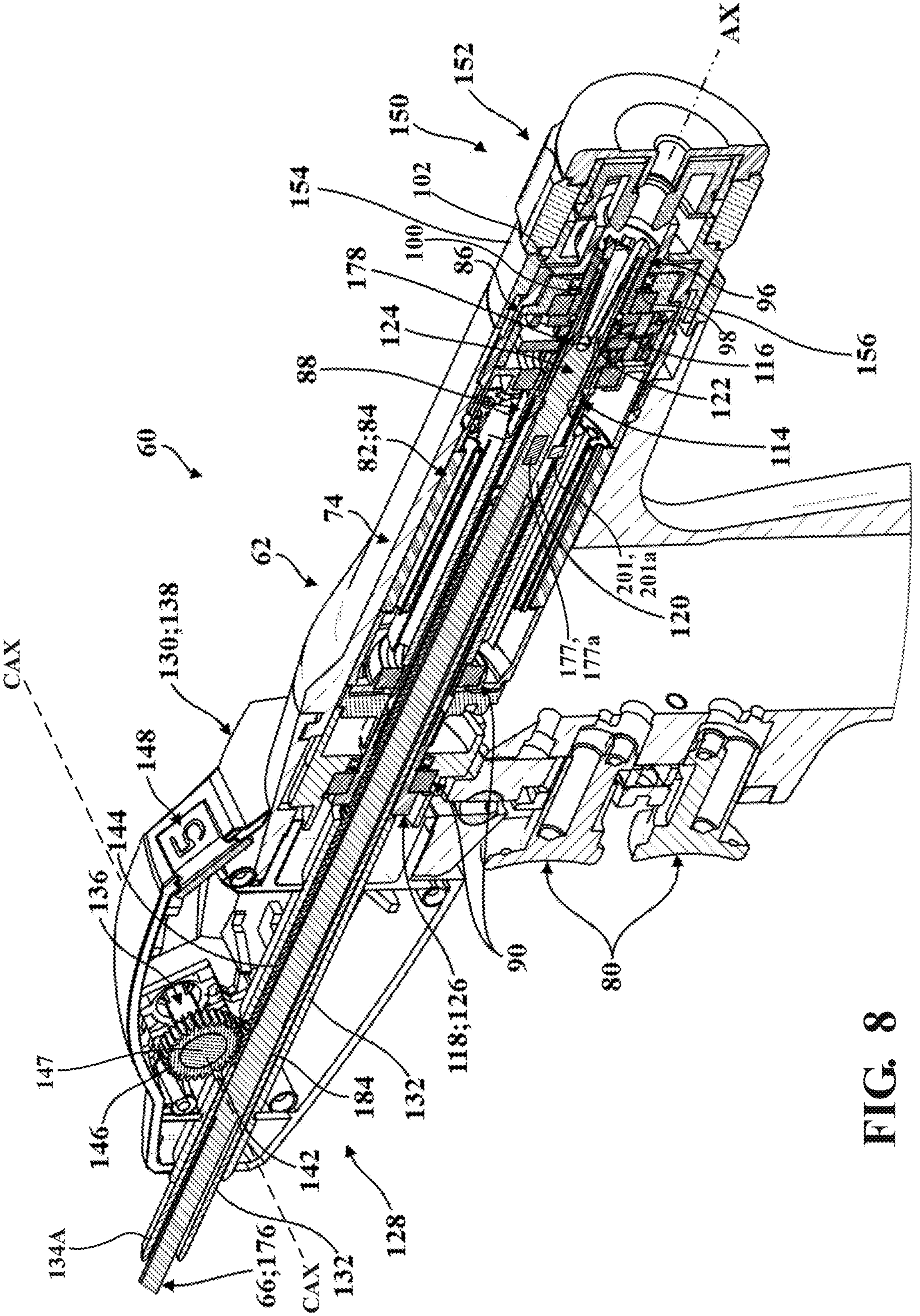
FIG. 8 is a partial isometric sectional view taken along line 8-8 in FIG. 1 illustrating the arrangement of the identification feature and the sensor located within the handpiece body.
Figure 9:
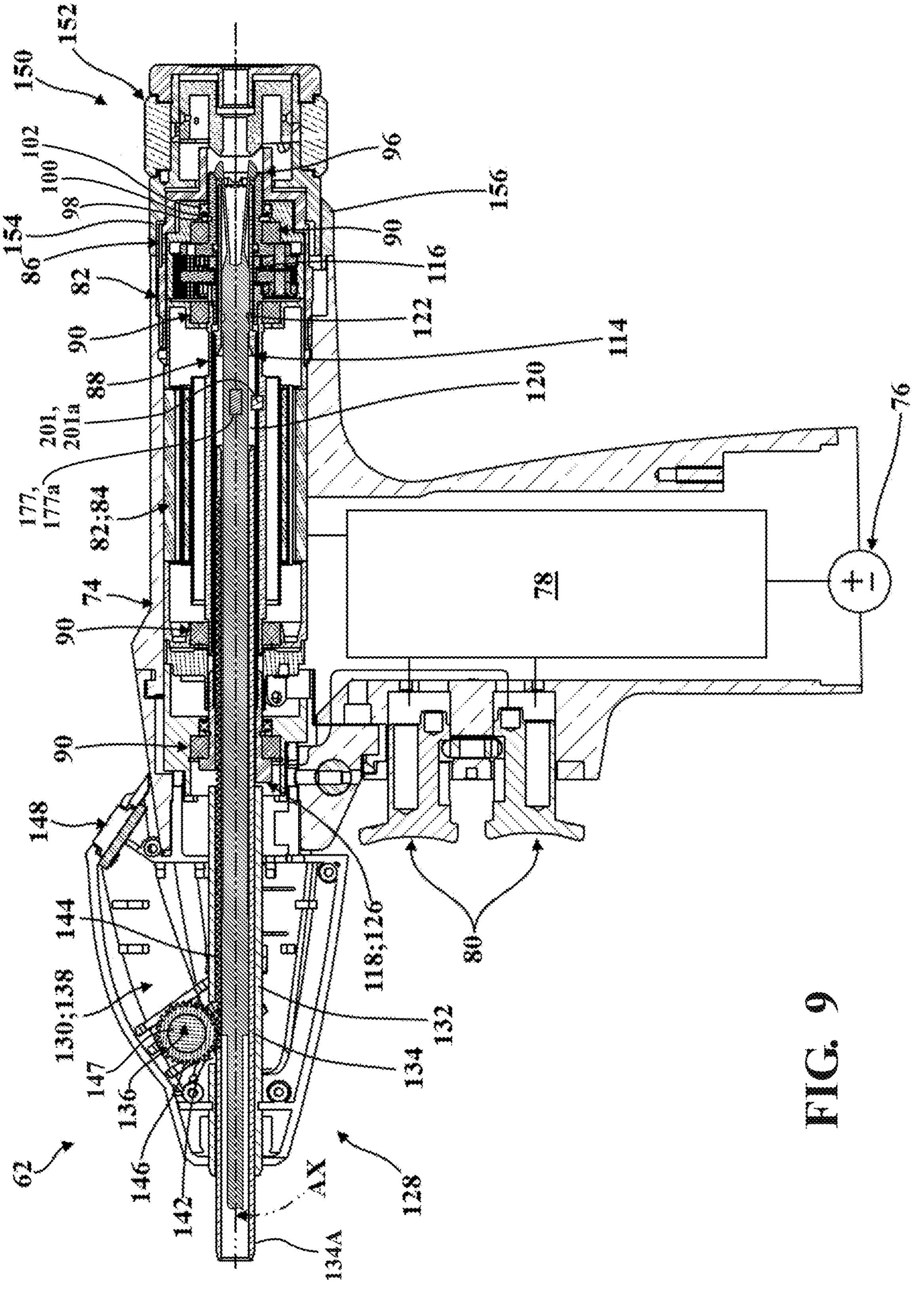
FIG. 9 is a sectional view taken longitudinally through the surgical instrument of FIG. 1 also illustrating the arrangement of the identification feature and the sensor located within the handpiece body.

For example, as illustrated in FIGS. 8 and 9, the sensor 201 may be coupled to, or carried within, the handpiece body 74 at a position in proximity to the identification feature 177/one or more magnets 181 such that the sensor 201 can sense the identification signal/magnetic field signal in the same manner as described above wherein the sensor 201 is contained within the measurement module 128 as in FIGS. 4 and 5. As best shown in FIGS. 8 and 9, the relative location of the identification features 177/one or more magnets 181 are disposed along the shank 176 of the drill bit 66 or within the sleeve 179 at a position nearer to the insertion portion 72 of the drill bit assembly 65 than their relative positioning in the drill bit assembly 65 used in FIGS.

4 and 5 so as to be aligned in a direction normal to the axis AX with the sensor 201 carried in the handpiece body 74. In certain configurations, such as shown in FIGS. 8 and 9, the sensor 201 is located within the handpiece body 74 at a position that is not aligned with the guide bushing 132 in a direction normal to the axis AX depending upon the operation of the surgical drill system 60.

More specifically, depending upon the positioning of the measurement cannula 134 relative to sensor 201 within the housing 130 in FIGS. 4 and 5, or relative to the sensor 201 in the handpiece body 74 in FIGS. 8 and 9, a portion of the measurement cannula 134 may or may not be disposed between the identification features 177 and the sensor 201 in a direction normal to the axis AX. In these examples, the measurement cannula 134 may be biased forward with the gear 136 and a biasing member (e.g., a torsion spring) such that the measurement cannula 134 may be biased to the fully distal position, and be under tension while the measurement cannula 134 is proximal of the fully distal position.

Figure 10B:
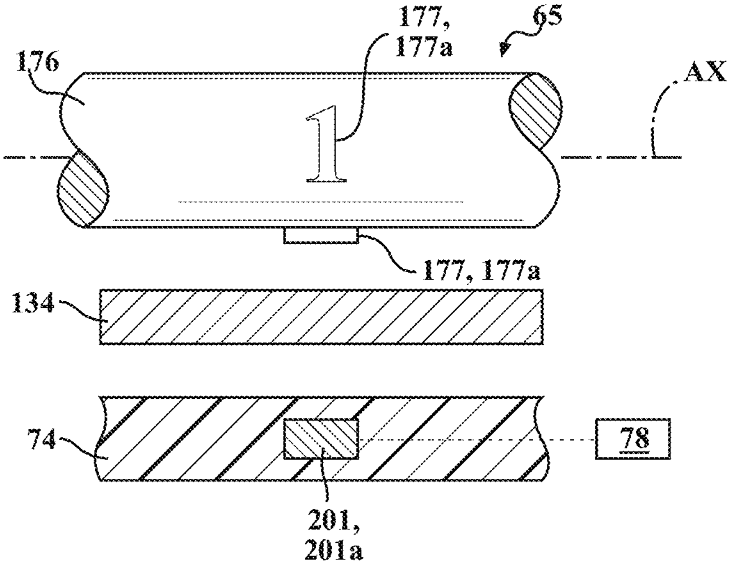
FIG. 10B is a partial schematic view of the drill bit, identification feature, measurement cannula, and sensor of FIG. 4-5 or 8-9 with the measurement cannula in a fully distal position.
Figure 10C:
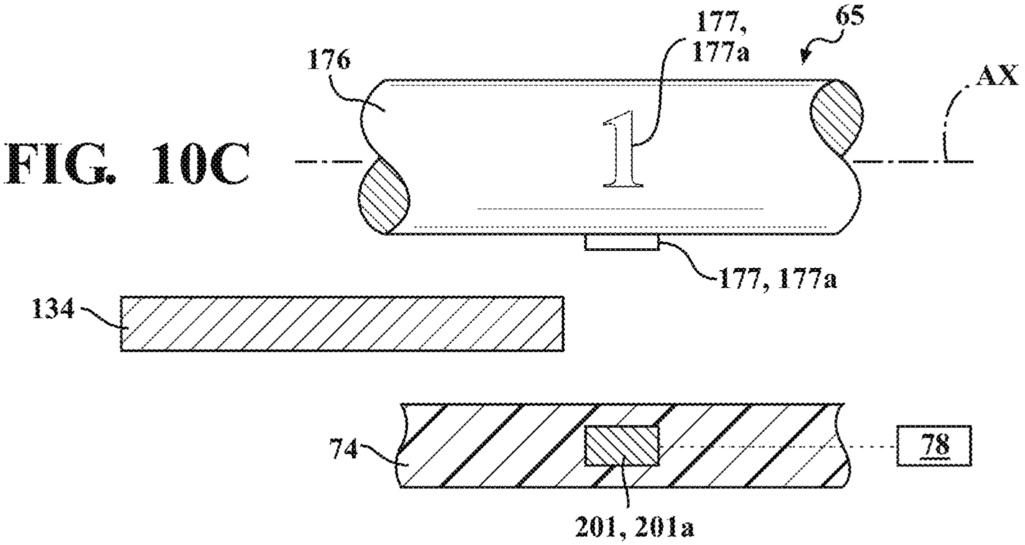
FIG. 10C is a partial schematic view of the drill bit, identification feature, measurement cannula, and sensor of FIG. 4-5 or 8-9 with the measurement cannula in proximal position relative to the fully distal position.

In certain configurations, the sensor 201 is located in the measurement module 128 in location such that the sensor 201 is proximal the proximal end of the measurement cannula 134 when the measurement cannula 134 is in the fully distal position. In configurations where the sensor 201 is located within the measurement head 128 and the measurement cannula 134 is proximal to the fully distal position, as shown in FIG. 10B, the sensor 201 may be located such that the measurement cannula 134 is between the sensor 201 and identification features 177. Further, when the measurement cannula 134 is moved back to a fully distal position, as shown in FIG. 10C (wherein the measurement cannula 134 has moved distal relative to positioning of the measurement cannula 134 FIG. 10B), the sensor 201 may be located such that the measurement cannula 134 is not disposed between the sensor 201 and the identification features 177. In either scenario, the sensor 201 can sense the identification feature as the drill bit assembly 65 rotates 360 degrees around the axis AX.

Accordingly, the configuration provided in FIGS. 10A-10C allows the use of other kinds of sensors 201 and associated identification features 177 that cannot otherwise be sensed through the measurement cannula 134 or guide bushing 302. For example, FIGS. 10A-C illustrates an alternative configuration wherein the sensor 201 is in the form of an optical sensor 201*a*, and the identification features 177 are in the form of laser etchings, printings, or other optical indicia (laser printings 177*a* in the shape of a "1" are illustrated in FIGS. 10A-10C). In these configurations, the optical sensor 201*a* can sense the individual laser printings 177*a* as the drill bit assembly 65 is stationary or rotating 360 degrees about axis AX. The positioning of the sensor 201 as illustrated in FIGS. 10A-10C thus also allow the use of identification features 177*a* and sensors 201*a* that cannot typically be utilized when a guide bushing 132 or measurement cannula 134 is disposed therebetween, unless the measurement cannula is transparent. The optical identification features, such as the laser etchings, printings or other markings may be formed on a substrate that is coupled to the drill bit. The substrate may take the form of a heat-sensitive label. The substrate may be adhered to the drill bit with an adhesive. Similar to the array of magnets, the optical identification feature may comprise one or more arrays of optical indicia that may aligned in an orientation about the axis AX to present unique identification of the drill bit 66 or drill bit assembly 65.

If the substrate takes the form of a heat-sensitive label, it is foreseeable that the optical features would no longer be discernable after the drill bit is sterilized at temperatures above 120 degrees C. in certain configurations.

As shown in FIGS. 10A-10C, the optical sensor 201*a* may include an emitter (i.e., light source) and a receiver, and one or more lenses to gather light reflected by the optical identification feature 177*a* of the drill bit assembly 65. In certain configurations, the optical sensor 201*a* may also include a light emitting diode (LED) and a phototransistor that work together to respectively emit light onto the drill bit 66 and measure the light reflectance occurring. Due to the shape of the drill bit 66 and its reflective properties, including with the identification features 177*a*, the emitter and receiver of the sensor 201 may be configured to lie on the same plane, parallel to the drill bit 66. In these configurations, the identification features 177*a* (such as the laser markings 177*a* shown in FIGS. 10A-10C) will intentionally scatter light away from the receiver, resulting in a lower signal in contrast to the strong reflections of light along the shank 176 that do not include such identification features 177*a*.

In addition to a phototransistor, other configurations of detecting reflected light off the drill bit 66 are contemplated. For high resolution detection, an optical sensor 201*a* similar to a camera could be used to obtain a full image of the identification feature 177*a*, as opposed to a digital signal. Other potential methods of light detection using an optical sensor 201*a* include visible light spectrum LED or vertical cavity surface emitting laser (VCSEL). In particular, a VCSEL could provide additional advantages in terms of power efficiency and light focusing. Yet still further, other solutions for focusing emitted light for detection by the optical sensor 201*a* include providing an aperture built into a plastic bushing and reducing the wide emission angle of an LED when utilized.

The controller 78 comprises one or more microprocessors having a memory unit for processing instructions or for processing algorithms stored in memory to carry out the functions described herein. Additionally or alternatively, the controller 78 may comprise one or more microcontrollers, subcontrollers, field programmable gate arrays, systems on a chip, discrete circuitry, and/or other suitable hardware, software, or firmware that is capable of carrying out the functions described herein. For instance, the controller may be disposed in the measurement module 128 and a second controller (e.g., a subcontroller, a processor, etc.) may be disposed in the handpiece 62. The second controller may be configured to generate signals to the motor of the handpiece 62 to operate the motor. More specifically, the second controller may control a relative amount of torque generated by the motor on the basis of the transducer signal and the identification signal received by the first controller 78 in the measurement module 128. The controller 78 may be carried in the handpiece body 74 as illustrated in FIG. 5, or elsewhere in the surgical drill system 60, such as on the measurement head 128 or may be remotely located. Memory may be any memory suitable for storage of data and computer-readable instructions (i.e., readable code). For example, the memory may be a local memory, an external memory, or a cloud-based memory embodied as random access memory (RAM), non-volatile RAM (NVRAM), flash memory, or any other suitable form of memory.

In certain configurations, the controller 78 comprises an internal clock to keep track of time. For example, the internal clock may be a microcontroller clock. The microcontroller clock may comprise a crystal resonator; a ceramic resonator; a resistor, capacitor (RC) oscillator; or a silicon oscillator. Examples of other internal clocks other than those disclosed herein are fully contemplated. The internal clock may be implemented in hardware, software, or both. In some configurations, the memory, microprocessors, and microcontroller clock cooperate to send signals to and operate the various components to meet predetermined timing parameters.

The controller 78 is electrically coupled at least to each of the input control 80, actuator assembly 82, drive assembly 114, measurement module 128 (including the transducer assembly 136), and sensor 201 to control the operation of the surgical drill system 60.

In particular, the controller 78 may be configured to receive an identification signal from the sensor 201 generated by the identification feature 177 that is sensed by the sensor 201 when a respective drill bit assembly 65 is properly coupled to the coupler 26 and the housing 130 and wherein the drill bit 66 is rotating about the axis AX. The microprocessor of the controller 78 includes a memory unit that has been preprogrammed with an algorithm that includes a list of known identification signal signals, with each member of the list of known identification signals corresponding to a respective one of the one or more drill bits 66 or drill bit assemblies 65 having the unique identification feature 177. Accordingly, when the received identification signal is compared to the list of known identification signals, a match is confirmed (and hence one of the respective drill bit assemblies 65 that includes the identification feature 177 or unique configuration of magnets 181 is positively identified), the controller 78 may then control the operation of the surgical drill system 60 on the basis of the identified drill bit assembly 65.

By way of example, when the user operates the handpiece 62 such that the drill bit 66 is rotating about the axis AX, the algorithm is configured to process the change in the identification signal generated by the identification feature sensed by the sensor 201 and analyze the generated signal pattern, such as measuring time between the edges of the identification feature 177 or analyzing a binary pattern within a very fine time interval. The algorithm confirms the identification signal pattern for a few rotations of the drill bit 66. Once the pattern is detected and confirmed, the algorithm checks the pattern versus the list of known identification signal signals to identify a respective drill bit assembly 65 based on a match with the pattern from the list of known identification signals.

For example, when a match of the received identification signal to a known identification signal, or when a match of a received magnetic field signature signal to a known magnetic field signature signal (or magnetoresistance signature signal), is confirmed by the controller 78 on the basis of the coupled drill bit assembly 65, and typically displayed on the output device 148 for viewing by the operator, the user of the surgical drill system 60 can be confident that the drill bit assembly 65 coupled to handpiece 62 is properly positioned and has the known desired one or more identifiable performance features (i.e., the drill bit assembly 65 includes the identification feature 177/magnet 181 and has been identified by the controller 78 on the basis of length, diameter, flute design, material choice, and combinations thereof). This increase level of confidence also may increase the safety of the drilling operation.

Alternatively, when a match is not confirmed by the controller 78, indicating that the properly coupled drill bit assembly 65 has not been identified by the sensor 201 as corresponding to a known drill bit assembly 65, the lack of a match can also be displayed on the output device 148 for viewing by the operator, thereby confirming to the operator that the coupled drill bit assembly 65 has not been identified by the controller 78 on the basis of length, diameter, flute design, material choice, and combinations thereof. The lack of confirmation may be indicative that the coupled drill bit assembly is not a drill bit assembly 65 with the identification feature 177, regardless of whether the drill bit assembly 65 has been previously used or not. Alternatively, the lack of confirmation may be indicative that the drill bit assembly 65, while having the identification feature(s) 177 in the form of magnet(s) 181, has previously been used and has been reprocessed for subsequent use by heating the drill bit assembly 65 to a temperature sufficient to demagnetize the magnet(s) 181 and/or deform the sleeve 179 (when utilized). On this basis, the operator may then decide not to initiate a bone drilling operation using the coupled, but unidentified, drill bit assembly 65.

In addition to identifying the coupled drill bit assembly 65, the controller 78 may also be configured to receive a transducer signal, sometimes alternatively referred to as a displacement signal, from the transducer assembly 136 corresponding to the relative positioning of the distal end 134A of the measurement cannula 134 relative to the housing 130. The controller 78 in turn, is configured to control the transfer of torque from the handpiece 62 to the coupled drill bit assembly 65 to the workpiece on the basis of the identification signal and further on the basis of the received transducer signal.

In particular, the controller 78 may also be configured to determine an acceleration signal based on movement of a depth measurement extension, such as the movement of the distal end 134A of the measurement cannula 134 (as provided herein), corresponding to the received transducer signal, during a time within a first time interval. On the basis of the determined acceleration signal, the controller 78 may be further configured to determine a breakthrough depth of the coupled drill bit assembly 65 through the workpiece. In particular, the controller 78 determines a breakthrough time (Tb) of the drill bit 66 through the workpiece within the first time interval based on the acceleration signal. From this information, and in conjunction with the received transducer signal and the received identification signal, the controller 78 uses an algorithm to determine a depth of the bore hole i.e., drilling passage, in the workpiece.

Accordingly, the controller 78 may then be further configured to control the transfer of torque to the coupled and identified replaceable drill bit assembly 65 to precisely control the drilling of a hole in the workpiece to a predetermined and desired depth and bore diameter.

Figure 17A:
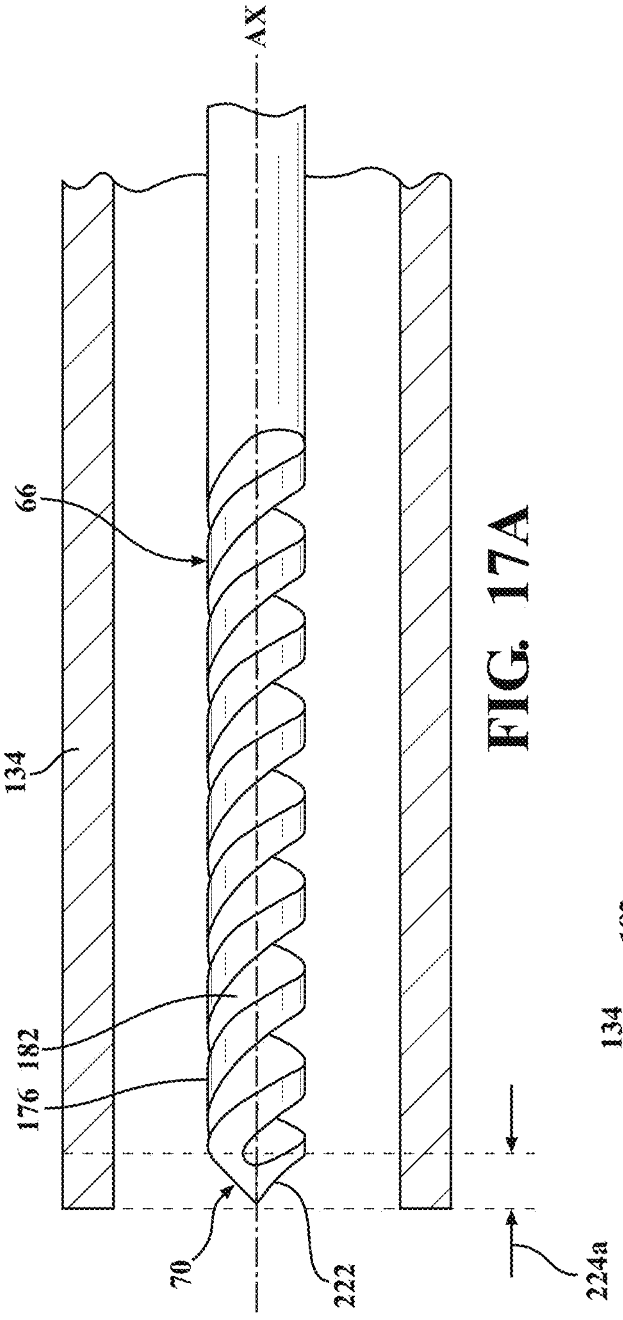
FIG. 17A is an elevation view of a measurement cannula and a drill bit having a first point length.
Figure 17B:
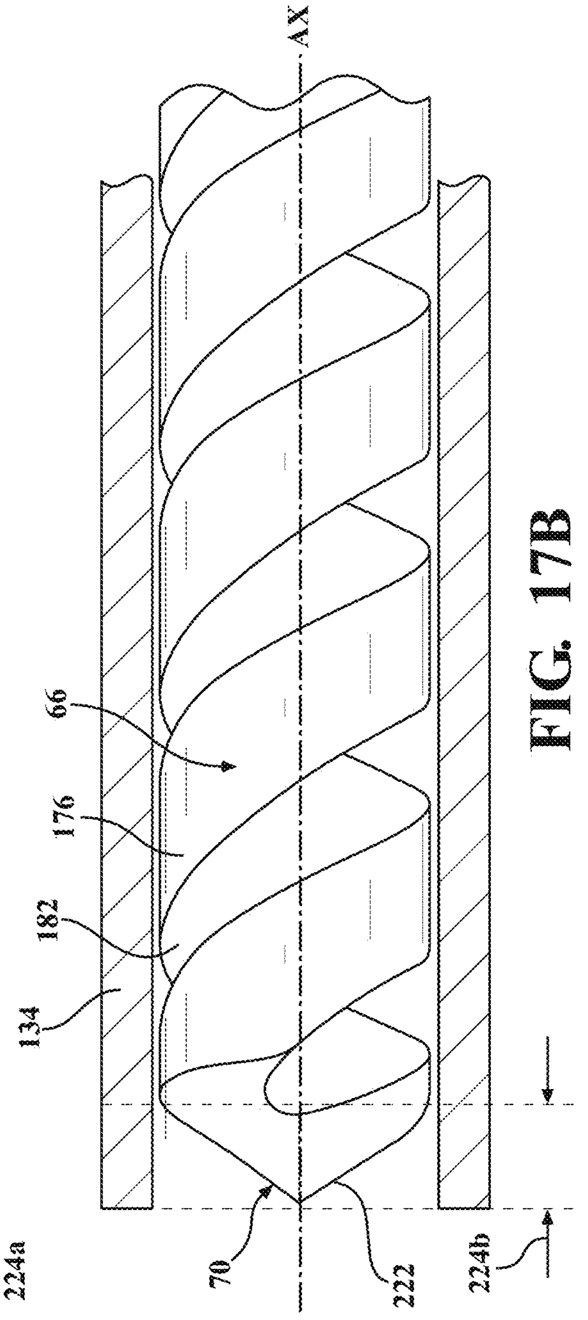
FIG. 17B is an elevation view of a measurement cannula and a drill bit having a second point length.

In one configuration illustrated in FIGS. 17A and 17B, the controller 78 may use the identity of the drill bit 66 to determine an offset to apply to a breakthrough depth determined from one or more signals received from the transducer assembly 136. The cutting tip portion 70 of the drill bit 66 may have a drill bit point 222 extending proximally along the axis AX from the distal end of the drill bit 66. The drill bit point 222 tapers away from the axis from the distal end of the drill bit 66 to the distal end 180 of the shank 176 where at least a distal portion of the shank comprises a generally cylindrical body. The drill bit point 222 may have a point length 224*a*, 224*b* extending along the axis AX between the distal end of the drill bit 66 and the distal end of the shank 176. Drill bit points 222 and corresponding point lengths 224*a*, 224*b* may vary from drill bit 66 to drill bit 66. In some configurations, the wider a diameter of the distal end 180 of the shank 176 is, the longer the point length 224*a*, 224*b* will be. In many configurations, the drill bit breakthrough depth is determined when the distal end 180 of the shank 176 breaks through a desired medium. Different point lengths 224*a*, 224*b* may result in different signals being generated by the transducer assembly 136 for breakthrough depth when the breakthrough depths should be identical. In one configuration, the point length 224*a* of the drill bit 66 shown in FIG. 17A is smaller than the point length 224*b* of the drill bit 66 shown in FIG. 17B. When each drill bit 66 is place against a drilling medium, the measurement cannula 134 in the configuration of 17B will be displaced a greater distance than the measurement cannula 134 shown in FIG. 17A because the drill bit 66 in FIG. 17B will need to drill a greater distance for the distal end 180 of the shank 176 to break through. An offset value may be used by the controller 78 to add or subtract from a displacement value of the measurement cannula 134 determined from the transducer signal to provide an accurate value of breakthrough depth.

In an exemplary configuration, the sensor 201 may generate an identification signal responsive to an identification feature 177 of the drill bit 66 to identify the point length 124*a*, 124*b* of the drill bit 66 coupled to the handpiece 62. The controller 78 may receive the identification signal and the transducer signal from the transducer assembly 136 to identify a point length of the drill bit 66 and to determine a breakthrough depth of a borehole or drilling passage based on the point length 224*a*, 224*b* of the drill bit 66 and displacement of the measurement cannula 134. The output device 148 may display information pertaining to an offset value associated with the coupled drill bit 66, a displacement value of the measurement cannula 134, and/or a breakthrough depth determined by the controller 78 based on the offset value and the displacement value.

In another configuration, the surgical handpiece system 60 may be configured to determine a suitable screw length for bone fixation with a bone plate that compensates an initial screw length or displacement value. The memory of the controller 78 may store information relating to certain bone plate thicknesses commonly or exclusively associated with certain drill bits 66. When the controller 78 identifies the drill bit 66 from the identification signal from the sensor 201, the controller 78 may determine from the identification signal that a certain bone plate may be associated with the coupled drill bit 66. The controller 78 may receive the transducer signal from the transducer assembly 136 to determine a screw length based on the bone plate thickness associated with the bone plate corresponding to the coupled drill bit 66 and displacement of the measurement cannula 134. The output device 148 may display a screw length, a bone plate thickness, a type of bone plate, displacement of the measurement cannula 134, and/or a breakthrough depth value based on the thickness of the bone plate and the displacement of the measurement cannula 134.

The predetermined bore depth and bore diameter within the workpiece will allow for the subsequent placement of a properly sized screw or other fastening device that is fitted with the drilled bore. In particular, the determined depth and diameter of the bore hole can be indicated on the display screen of the output device 148 viewable by the operator, with such information being used by the operator to determine a properly sized screw fitted for the drilled bore.

Several configurations have been discussed in the foregoing description. However, the configurations discussed herein are not intended to be exhaustive or limit the disclosure to any particular form. Other configurations are specifically contemplated. The terminology which has been used is intended to be in the nature of words of description rather than of limitation. Many modifications and variations are possible in light of the above teachings and the disclosure may be practiced otherwise than as specifically described.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

The disclosure is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses that may specifically be implemented as described in greater detail with reference to the configurations and drawings above.

Clauses

I. A drill bit for use on a surgical drill, the drill bit comprising:
   a shank extending between a proximal end and a distal end extending along an axis;
   a cutting tip portion adjacent to the distal end of the shank;
   a sleeve disposed about at least a portion of the shank, the sleeve comprising a material having a glass transition temperature at or below 120 degrees Celsius or a heat sensitive label disposed about at least a portion of the shank, the sleeve or the heat sensitive label comprising an optical identification feature for identifying a configuration of the cutting tip portion.

II. The drill bit of clause I, wherein the sleeve defines a lumen sized to be disposed over the shank of the drill bit.

III. The drill bit of any one of clauses I or II, wherein the optical identification feature comprises an array of optical indicia disposed circumferentially about the shank.

IV. The drill bit of clause III, wherein a first optical indicia of the array of optical indicia is different in size, shape, angular spacing, or combinations thereof than a second optical indicia of the array of optical indicia.

V. The drill bit of clause III or IV, wherein angular spacing between a first optical indicia of the array of optical indicia and a second optical indicia of the array of optical indicia is the same as angular spacing between the second optical indicia and a third optical indicia of the array of optical indicia.

VI. The drill bit of any one of clauses III-V, wherein angular spacing between a first optical indicia of the array of optical indicia and a second optical indicia of the array of optical indicia is different than angular spacing between the second optical indicia and a third optical indicia of the array of optical indicia.

VII. The drill bit of any one of clauses III-VI, wherein the array of optical indicia is further defined as the first array of optical indicia, and wherein the optical identification feature comprises a second array of optical indicia disposed circumferentially about the shank and disposed spaced from the first array of optical indicia.

VIII. The drill bit of clause VII, wherein each of the first array of optical indicia and the second array of optical indicia comprise the same number of optical indicia.

IX. The drill bit of any one of clauses VII or VIII, wherein at least one optical indicia in the first array of optical indicia is angularly aligned with an optical indicia in the second array of optical indicia in a direction parallel to axis of the shank.

X. The drill bit of clause VII-IX, wherein at least one optical indicia in the first array of optical indicia is not angularly aligned with any of the optical indicia of the second array of optical indicia.

XI. A measurement module configured to be coupled to a surgical handpiece and configured for use with a drill bit having an identification feature, the measurement module comprising:
- a housing;
- a measurement cannula comprising a non-magnetic material, the measurement cannula configured to circumferentially surround the drill bit when the drill bit is coupled to the handpiece, and the measurement cannula is slidably mounted to the housing so as to extend forward or rearward relative to the housing between a fully distal and a proximal position, and the measurement cannula having a distal end adapted for placement against a workpiece;
- a transducer assembly for generating a transducer signal based on a position of the distal end of the measurement cannula relative to the housing; and
- a sensor for generating a signal responsive to a magnetic field or magnetoresistance of the identification feature of the drill bit through the measurement cannula when the drill bit is coupled to the handpiece and rotating about an axis.

XII. A measurement module configured to be coupled to a surgical handpiece and configured for use with a drill bit having an identification feature, the measurement module comprising:
- a housing;
- a depth measurement extension moveable relative to the housing;
- a transducer assembly for generating a transducer signal based on a position of a distal end of the depth measurement extension relative to the housing;
- a sensor for generating an identification signal based on the identification feature of the drill bit as the drill bit rotates about an axis; and
- a controller configured to determine a breakthrough depth of a drill passage based on receipt of the generated transducer signal and the generated identification signal.

XIII. The measurement module of clause XII, wherein the performance feature is selected from a group consisting of a length, a material, a diameter, a cross-sectional area, a type, a cutting efficiency, a rake angle, a flute angle, a point angle and combinations thereof.

XIV. A measurement module configured to be coupled to a surgical handpiece and configured for use with a drill bit, the measurement module comprising:
- a housing;
- a depth measurement extension moveable relative to the housing;
- a transducer assembly for generating a transducer signal based on a position of a distal end of the depth measurement extension relative to the housing; and
- a controller configured to determine a breakthrough depth of a drill passage based on receipt of the generated transducer signal and a performance feature of the drill bit being used with the surgical handpiece.

XV. The measurement module of clause XIV, wherein the performance feature is selected from a group consisting of a length, a material, a diameter, a cross-sectional area, a type, a cutting efficiency, a rake angle, a flute angle, a point angle and combinations thereof.

XVI. A surgical handpiece system for use with a drill bit having an identification feature, the surgical handpiece system comprising:
- a handpiece for coupling the drill bit and for transferring torque to the coupled drill bit to rotate the drill bit about an axis;
- a measurement module coupled to the handpiece, the measurement module comprising, a housing,
- a measurement cannula moveable relative to the housing to a fully distal position and to a proximal position,
- a biasing member configured to bias the measurement cannula to the fully distal position;
- a transducer assembly for generating a transducer signal based on a position of the distal end of the measurement cannula relative to the housing; and
- a sensor for generating an identification signal based on an identification feature of the coupled drill bit, the sensor being located within the housing in a position such that the sensor is proximal to the proximal end of the measurement cannula when the measurement cannula is in the fully distal position.

XVII. The surgical handpiece system of clause XVI, wherein the sensor is an optical sensor.

XVIII. The surgical handpiece system of any one of clauses XVI or XVII, wherein the sensor is selected from a group consisting of a magnetic field sensor, a hall effect sensor, and a magnetoresistance sensor.

XIX. A measurement module configured to be coupled to a surgical handpiece and configured for use with a drill bit having an identification feature, the measurement module comprising:
- a housing;
- a measurement cannula moveable to a fully distal position and to a proximal position;
- a biasing member configured to bias the measurement cannula to the fully distal position;
- a transducer assembly for generating a transducer signal based on a position of the distal end of the measurement cannula relative to the housing;
- a sensor for generating an identification signal based on the identification feature of the drill bit when the drill bit is coupled to the handpiece and the coupled drill bit rotates about an axis, the sensor being disposed within the housing and configured to be proximal of a proximal end of the measurement cannula when the measurement cannula is in the fully distal position.

XX. A surgical handpiece system for use with a drill bit having an identification feature, the surgical handpiece system comprising:
- a handpiece for coupling the drill bit and for transferring torque to the drill bit and configured to rotate the drill bit about an axis;
- a measurement module coupled to the handpiece, the measurement module comprising, a housing, and
- a measurement cannula, the measurement cannula configured to at least partially circumferentially surround the drill bit when the drill bit is coupled to the handpiece, and the measurement cannula slidably mounted to the housing so as to extend forward or rearward relative to the housing between a fully distal position and a proximal position, and the measurement cannula having a distal end adapted for placement against a workpiece;

a transducer assembly for generating a transducer signal based on a position of the distal end of the measurement cannula relative to the housing; and a sensor for sensing an identification feature of the drill bit through the measurement cannula when the drill bit is coupled to the handpiece and rotating about the axis.

XXI. The surgical handpiece system of clause XX, wherein the sensor is selected from a group consisting of a magnetic field sensor, a hall effect sensor, and a magnetoresistance sensor.

XXII. A drill bit for use on a surgical drill having a magnetoresistance sensor for generating signals responsive to variations in a magnetic field, the drill bit comprising: a shank extending between a proximal end and a distal end along an axis, the shank configured to rotate about the axis, and the shank having an outer surface defining one or more recesses to establish a non-circular cross-section on a plane perpendicular to the axis such that a radial distance between the outer surface and the axis varies about the axis, and the shank configured to effect variations in the magnetic field during rotation of the shank about the axis responsive to the varying radial distances of the outer surface to the axis; and a cutting tip portion adjacent to the distal end of the shank;

wherein the one or more recesses of the outer surface of the shank comprises an identification feature for identifying one or more performance features of the cutting tip portion.

XXIII. The drill bit of clause XXII, further comprising a coupling portion proximal of the shank and the cutting tip portion, the coupling portion configured to engage the surgical drill to couple the drill bit to the surgical drill.

XXIV. The drill bit of clause XXII or XXIII, wherein the performance feature of the cutting tip portion is selected from the group consisting of a length, a material, a diameter, a cross-sectional area, a type, a rake angle, a flute angle, point angle, and combinations thereof.

XXV. The drill bit of any one of clauses XXII-XXIV, wherein the outer surface of the shank further defines the one or more recesses as an array of outer recess disposed circumferentially about the shank.

XXVI. The drill bit of clause XXV, wherein at least one recess of the array of recesses is different in depth, arc length, or combinations thereof than at least one other recess of the array of recesses.

XXVII. The drill bit of clause XXV or XXVI, wherein angular spacing between a first recess of the array of the recesses and a second recess of the array of recesses is the same as angular spacing between the second recess and a third recess of the array of recesses.

XXVIII. The drill bit of any one of clauses XXV-XXVII, wherein angular spacing between a first recess of the array of the recesses and a second recess of the array of recesses is different than angular spacing between the second recess and a third recess of the array of recesses.

XXIX. The drill bit of any one of clauses XXV-XXVIII, wherein a size of one recess of the array of recesses is greater than a size of one or more other recesses of the array of recesses.

XXX. The drill bit of any one of clauses XXV-XXIX, wherein the array of recesses is further defined as a first array of recess and the outer surface further defines a second array of recesses disposed circumferentially about the shank and disposed axially spaced from the first array of recesses.

XXXI. The drill bit of clause XXX, wherein each of the first array of recesses and the second array of recesses defines the same number of recesses.

XXXII. The drill bit of any one of clauses XXX-XXXI, wherein at least one recess of the first array of recesses is angularly aligned with a recess in the second array of recesses in a direction parallel to the axis of the shank.

XXXIII. The drill bit of clause XXX-XXXII wherein at least one recess in the first array of recesses is not angularly aligned with any of the recesses in the second array of recesses in a direction parallel to the axis of the shank.

XXXIV. A method of making a drill bit assembly having magnetic identification features comprising:

providing a drill bit having a shank and a cutting tip portion, the drill bit being disposed along an axis;

disposing one or more magnets adjacent the shank of the drill bit; and molding nonmagnetic material around at least part of the shank and the one or more magnets to secure the one or more magnets to the shank of the drill bit.

XXXV. A surgical handpiece system comprising:

a handpiece;

a drill bit configured to be coupled to the handpiece and to receive torque from the handpiece to rotate about an axis, the drill bit comprising, a shank extending between a proximal end and a distal end along the axis, the shank configured to rotate about the axis, and the shank having an outer surface defining one or more recesses to establish a non-circular cross-section on a plane perpendicular to the axis such that a radial distance between the outer surface and the axis varies about the axis, a cutting tip portion adjacent to the distal end of the shank, wherein the one or more recesses of the outer surface of the shank comprises an identification feature for identifying one or more performance features of the cutting tip portion; and a measurement module configured to be coupled to the handpiece, the measurement module comprising, a housing configured to be coupled to the handpiece, and a measurement cannula being slidably mounted to the housing so as to extend forward or rearward relative to the housing between a fully distal position and a proximal position, the measurement cannula having a distal end adapted for placement against a work-piece, wherein one of the measurement module and the handpiece comprises a sensor for generating an identification signal responsive to variations in a magnetic field during rotation of the shank about the axis resulting from varying radial distances of the outer surface to the axis for identifying the configuration of the cutting tip portion of the drill bit.

XXXVI. The surgical handpiece system of clause XXXV, wherein the measurement cannula comprises a nonmagnetic material, and wherein the handpiece comprises a body and the sensor is disposed in the body of the handpiece such that the measurement cannula is disposed between the sensor and the identification feature in a direction normal to the axis in the proximal position and such that the measurement cannula is not disposed between the sensor and the identification feature in the direction normal to the axis in the fully distal position.

XXXVII. The surgical handpiece system of any one of clauses XXXV-XXXVI, wherein the non-magnetic material comprises a polymeric material.

XXXVIII. The surgical handpiece system of any one of clauses XXXV-XXXVII, further comprising a controller configured to receive the identification signal and identify the coupled drill bit corresponding to the received identification signal.

XXXIX. The surgical handpiece system of clause XXXVIII, further comprising a transducer assembly for generating a transducer signal based on a position of the distal end of the measurement cannula relative to the housing.

XL. The surgical handpiece system of clause XXXIX, wherein the controller is configured for receiving the generated transducer signal and controlling a relative amount of torque transferring to the drill bit on the basis of the received transducer signal and the identification signal.

XLI. The surgical handpiece system of any one of clauses XXXIX-XL, wherein the controller is further defined as a first controller, and wherein the surgical handpiece system comprises a second controller, the first controller disposed in the measurement module and the second controller disposed in the handpiece, and the handpiece further comprising a motor for generating torque, the second controller configured for controlling a relative amount of torque generated by the motor on the basis of the transducer signal and the identification signal.

XLII. The surgical handpiece system of any one of clauses XXXIX-XLI, wherein the measurement module further comprises a guide bushing circumferentially surrounding the measurement cannula, the guide bushing defining a window, with the transducer assembly being coupled to the measurement cannula through the window.

XLIII. The surgical handpiece system of any one of clauses XXXVIII-XLII, wherein the controller comprises a microprocessor having a memory unit, the memory unit including a list of known identification signals, with each respective one of the known identification signals of the list corresponding to a respective one known drill bit, the microprocessor configured for identifying the coupled drill bit by comparing the received identification signal to the list of known identification signals.

XLIV. The surgical handpiece system of any one of clauses XXXVIII-XLIII, wherein the identification signals differ from one another based on size, polarity, phase offset, strength, or combinations thereof.

XLV. The surgical handpiece system of clauses XXXV-XLIV, wherein the measurement module is integral with the handpiece.

XLVI. The surgical handpiece system of clauses XXXV-XLV, wherein the measurement module is removable from the handpiece.

XLVII. A surgical handpiece system configured to determine a breakthrough depth of a drilling passage for drill bits having unique identification features, the surgical handpiece system comprising:

a handpiece;

a drill bit extending from a proximal end to a distal end along an axis, the drill bit configured to be coupled to the handpiece and to receive torque from the handpiece to rotate about an axis, and the drill bit comprising a shank having an identification feature;

a measurement module configured to be coupled to the handpiece, the measurement module comprising, a housing configured to be coupled to the handpiece, a depth measurement extension being slidably mounted to the housing so as to extend forward or rearward relative to the housing between a fully distal position and a proximal position, the depth measurement extension having a distal end adapted for placement against a workpiece;

a transducer assembly for generating a transducer signal based on a position of a distal end of the depth measurement extension relative to the housing;

a sensor for generating an identification signal based on the identification feature of the drill bit when the drill bit is coupled to the handpiece; and a controller configured to receive the transducer signal and the identification signal and to determine the breakthrough depth of the drilling passage based on receipt of the generated transducer signal and the generated identification signal.

XLVIII. The surgical handpiece system of clause XLVII, wherein the transducer signal is responsive to a linear displacement of the depth measurement extension relative to an initial displacement position during use.

XLIX. The surgical handpiece system of any one of clauses XLVII or XLVIII, wherein the drill bit comprises a cutting tip portion having a drill bit point extending proximally along the axis from the distal end of the drill bit, the drill bit point tapering away from the axis from the distal end of the drill bit to the shank, the drill bit point having a point length along the axis between the distal end and the shank.

L. The surgical handpiece system of clause XL, wherein the shank of the drill bit extends proximally along the axis from the drill bit point to a proximal end of the drill bit, the shank of the drill bit comprises a cylindrical body having a continuous diameter along at least a portion of a length of the shank extending from the drill bit point.

LI. The surgical handpiece system of any one of clauses XLIX-L clause, wherein the identification signal corresponds to the point length of the drill bit, and wherein the breakthrough depth is based on the point length of the drill bit.

LII. The surgical handpiece system of any one of clauses XLIX-LI, wherein the controller comprises a microprocessor having a memory unit, the memory unit including a list of known identification signals, with each respective one of the known identification signals of the list corresponding to a respective one known drill bit having a known point length, the microprocessor configured for identifying the drill bit and the point length by comparing the received identification signal to the list of known identification signals when the drill bit is coupled to the handpiece.

LIII. The surgical handpiece system of any one of clauses XLVII-LII, wherein the depth measurement extension comprises a measurement cannula configured to circumferentially surround the drill bit when the drill bit is coupled to the handpiece.

LIV. The surgical handpiece system of any one of clauses XLVII-LIII, wherein the sensor is located within the housing of the measurement module.

LV. The surgical handpiece system of any one of clauses XLVII-LIV, wherein the sensor is located within a body of the handpiece.

VI. The surgical handpiece system of any one of clauses XLVII-LV, wherein the sensor is selected from the group consisting of an optical sensor, a magnetic field sensor, a hall effect sensor, and a magnetoresistance sensor.

LVII. The surgical handpiece system of any one of clauses XLVII-LVI, wherein the transducer assembly comprises at least one sensor selected from the group consisting of a potentiometer, an optical sensor, and a linear variable displacement transformer.

LVIII. The surgical handpiece system of any one of clauses XLVII-LVI, wherein the controller is disposed in the housing of the measurement module.

LIX. The surgical handpiece system of any one of clause XLVII-LVIII, wherein the measurement module is integral with the handpiece.

LX. The surgical handpiece system of clause XLVII-LIX, wherein the measurement module is removable from the handpiece.

LXI. A method of determining a breakthrough depth of a drilling passage during surgical drilling, the method comprising:
- providing a surgical handpiece system comprising a measurement module having a depth measurement extension;
- determining a displacement of the depth measurement extension during a surgical drill operation;
- identifying an identification feature on a drill bit with a sensor located in the surgical handpiece system; and
- determining a breakthrough depth of the drilling passage based on receipt of the displacement and the identification feature.

What is claimed is:

1. A surgical drill bit for use on a surgical drill, the surgical drill bit comprising:
- a shank extending between a proximal end and a distal end along an axis;
- a cutting tip portion adjacent to the distal end of the shank;
- a sleeve disposed about at least a portion of the shank, the sleeve comprising a non-magnetic material and an identification feature disposed about the shank for identifying a configuration of the cutting tip portion, the identification feature comprising a magnetic material dispersed in the non-magnetic material and configured for generating a magnetic field, the magnetic field being shaped asymmetrically about the axis of the shank, and wherein the magnetic material is configured to become at least partially demagnetized when heated to a temperature at or above 80 degrees Celsius.

2. The surgical drill bit of claim 1, wherein the magnetic material is uniformly dispersed in the non-magnetic material.

3. The surgical drill bit of claim 1, wherein the magnetic material comprises solid particles or flakes.

4. The surgical drill bit of claim 1, wherein a shape of a magnetic field generated by the sleeve is asymmetrical along the axis of the shank.

5. The surgical drill bit of 1, wherein the sleeve is divided into a first quadrant, a second quadrant, a third quadrant, and a fourth quadrant about the axis, and wherein a magnetic field generated by the first quadrant is different from the second quadrant, the third quadrant, and/or the fourth quadrant in terms of size, strength, polarity, or combinations thereof.

6. A surgical drill bit for use on a surgical drill, the surgical drill bit comprising:
- a shank extending between a proximal end and a distal end along an axis;
- a cutting tip portion adjacent to the distal end of the shank;
- a sleeve disposed about at least a portion of the shank, the sleeve comprising a non-magnetic material having a glass transition temperature at or below 120 degrees Celsius, and the sleeve comprising an identification feature for identifying a configuration of the cutting tip portion, the identification feature comprising a magnetic material;
- wherein the magnetic material is uniformly dispersed in the non-magnetic material such that no portion of the sleeve is more heavily concentrated with magnetic material than other portions of the sleeve.

7. The surgical drill bit of claim 6, wherein the magnetic material of the identification feature becomes at least partially demagnetized when heated to a temperature at or above 80 degrees Celsius.

8. The surgical drill bit of claim 6, wherein the magnetic material comprises solid particles or flakes.

9. The surgical drill bit of claim 6, wherein a shape of a magnetic field generated by the sleeve is asymmetrical about the axis of the shank.

10. The surgical drill bit of claim 6, wherein a shape of a magnetic field generated by the sleeve is asymmetrical along the axis of the shank.

11. The surgical drill bit of claim 6, wherein the sleeve is divided into a first quadrant, a second quadrant, a third quadrant, and a fourth quadrant about the axis, and wherein a magnetic field generated by the first quadrant is different from the second quadrant, the third quadrant, and/or the fourth quadrant in terms of size, strength, polarity, or combinations thereof.

12. A surgical drill bit assembly for use on a surgical drill, the surgical drill bit assembly comprising:
- a shank extending between a proximal end and a distal end along an axis;
- a cutting tip portion adjacent to the distal end of the shank; and
- a sleeve disposed about at least a portion of the shank, the sleeve comprising a non-magnetic material;
- the sleeve comprising an identification feature for identifying a configuration of the cutting tip portion, the identification feature comprising a magnetic material, wherein the magnetic material is uniformly dispersed in the non-magnetic material such that no portion of the sleeve is more heavily concentrated with magnetic material than other portions of the sleeve.

13. The surgical drill bit assembly of claim 12, wherein the magnetic material comprises solid particles or flakes.

14. The surgical drill bit assembly of claim 12, wherein a shape of a magnetic field generated by the sleeve is asymmetrical about the axis of the shank.

15. The surgical drill bit assembly of claim 12, wherein a shape of a magnetic field generated by the sleeve is asymmetrical along the axis of the shank.

16. The surgical drill bit assembly of claim 12, wherein the sleeve is divided into a first quadrant, a second quadrant, a third quadrant, and a fourth quadrant about the axis, and wherein a magnetic field generated by the first quadrant is different from the second quadrant, the third quadrant, and/or the fourth quadrant in terms of size, strength, polarity, or combinations thereof.

* * * * *